(12) United States Patent
Duarte et al.

(10) Patent No.: US 10,466,201 B2
(45) Date of Patent: Nov. 5, 2019

(54) COMPLEX IMPEDANCE MOISTURE SENSOR AND SENSING METHOD

(71) Applicant: PPG Industries Ohio, Inc., Cleveland, OH (US)

(72) Inventors: Nicolas B. Duarte, Allison Park, PA (US); Kurt G. Olson, Gibsonia, PA (US)

(73) Assignee: FPG Industries Ohio, Inc., Cleveland, OH (US)

( * ) Notice: Subject to any disclaimer, the term of this patent is extended or adjusted under 35 U.S.C. 154(b) by 0 days.

(21) Appl. No.: 15/886,132

(22) Filed: Feb. 1, 2018

(65) Prior Publication Data
US 2019/0234903 A1  Aug. 1, 2019

(51) Int. Cl.
*G01N 27/60* (2006.01)

(52) U.S. Cl.
CPC ..... *G01N 27/605* (2013.01); *G01N 2223/647* (2013.01)

(58) Field of Classification Search
CPC ................. G01N 27/605; G01N 2223/647
See application file for complete search history.

(56) References Cited

U.S. PATENT DOCUMENTS

| | | |
|---|---|---|
| 3,440,372 A | 4/1969 | Cecil |
| 3,710,244 A | 1/1973 | Rauchwerger |
| 4,078,107 A | 3/1978 | Bitterice et al. |
| 4,352,059 A * | 9/1982 | Suh ............. G01R 27/2647 204/430 |
| 4,522,060 A | 6/1985 | Murata et al. |
| 4,610,771 A | 9/1986 | Gillery |
| 4,623,389 A | 11/1986 | Donley et al. |
| 4,704,174 A | 11/1987 | Valimont et al. |
| 4,806,220 A | 2/1989 | Finley |
| 4,820,902 A | 4/1989 | Gillery |
| 4,894,513 A | 1/1990 | Koontz |
| 4,902,875 A | 2/1990 | Koontz |

(Continued)

FOREIGN PATENT DOCUMENTS

| | | |
|---|---|---|
| DE | 19518011 | 11/1996 |
| EP | 0564428 | 10/1993 |

(Continued)

*Primary Examiner* — Christopher P McAndrew
*Assistant Examiner* — Zannatul Ferdous
(74) *Attorney, Agent, or Firm* — Neil J. Friedrich

(57) ABSTRACT

An insulated pipe includes an elongated tube having a first end, a second end, and a sidewall extending therebetween; and an insulating member at least partially enclosing a portion of the sidewall, including at least one channel extending through at least a portion thereof. The insulated pipe also includes at least one coaxial moisture sensor positioned within at least a portion of the channel configured to sense moisture in the channel. The at least one coaxial moisture sensor includes: a dielectric member having a sleeve defining a center hole formed from an absorbent dielectric polymer material; an outer electrode electrically connected with an outer surface of the dielectric member including a moisture permeable sleeve which permits moisture to pass to the dielectric member; and an inner electrode having a wire extending through the center hole of and electrically connected with an inner surface of the dielectric member.

19 Claims, 10 Drawing Sheets

(56) References Cited

U.S. PATENT DOCUMENTS

| | | | |
|---|---|---|---|
| 4,994,650 A | 2/1991 | Koontz | |
| 5,028,906 A * | 7/1991 | Moriya | G01N 27/121 338/35 |
| 5,675,944 A | 10/1997 | Kerr et al. | |
| 5,821,001 A | 10/1998 | Arbab et al. | |
| 5,959,535 A | 9/1999 | Remsburg | |
| 6,826,948 B1 | 12/2004 | Bhatti et al. | |
| 8,155,816 B2 | 4/2012 | Rashid et al. | |
| 9,347,905 B2 | 5/2016 | Jiao et al. | |
| 9,975,646 B2 | 5/2018 | Jiao et al. | |
| 9,983,171 B2 | 5/2018 | Jiao et al. | |
| 2005/0115308 A1 * | 6/2005 | Koram | B32B 17/10036 73/73 |
| 2007/0002422 A1 | 1/2007 | O'Shaughnessy | |
| 2008/0223127 A1 | 9/2008 | Schmitt et al. | |
| 2010/0163675 A1 * | 7/2010 | Rashid | B32B 17/10009 244/129.3 |
| 2010/0264353 A1 * | 10/2010 | Hartmann | C08B 15/02 252/62 |
| 2011/0011179 A1 * | 1/2011 | Gustafsson | G01N 27/223 73/335.03 |
| 2012/0048038 A1 * | 3/2012 | Furlong | F16L 41/008 73/866.5 |
| 2012/0227484 A1 * | 9/2012 | Chen | A61M 1/28 73/304 R |
| 2014/0076048 A1 | 3/2014 | Gryska et al. | |
| 2015/0137837 A1 | 5/2015 | Jiao et al. | |
| 2015/0171624 A1 | 6/2015 | Duarte et al. | |
| 2015/0323491 A1 * | 11/2015 | Miller | G01N 33/24 205/789 |
| 2017/0030861 A1 * | 2/2017 | Jiao | B64D 45/00 |
| 2018/0017462 A1 | 1/2018 | Kube | |

FOREIGN PATENT DOCUMENTS

| | | |
|---|---|---|
| JP | 2007248409 A | 9/2007 |
| WO | 8103709 A1 | 12/1981 |
| WO | 2007009767 A2 | 1/2007 |
| WO | 2008047068 | 4/2008 |
| WO | 2015073269 A1 | 5/2015 |

* cited by examiner

COMPLEX IMPEDANCE MOISTURE SENSOR AND SENSING METHOD

FIELD OF THE INVENTION

This invention relates to devices having moisture sensors for sensing when moisture is present.

BACKGROUND OF THE INVENTION

Certain objects including, for example, building fixtures (e.g., pipes, insulation, electric wiring, and structural materials), vehicles (e.g., automobiles, airplanes, helicopters, drones, and ships), electronic devices (e.g., consumer appliances), and containers (e.g., storage tanks), include areas which should remain free from, or substantially free from, moisture. Such structures may be covered by a moisture resistive coating or enclosed within a housing to restrict or prevent ingression of moisture. In some cases, collected moisture could damage components contained within the housing or encapsulated by the coating. For example, electronic circuitry or components of electronic devices, such as consumer appliances, can be damaged when moisture leaks through and accumulates in the device housing. Performance of building materials, such as insulation, wood framing, bricks, stone, vinyl siding, composite wood materials, and others can also be reduced due to prolonged exposure to moisture or standing water. For example, thermal resistance of insulation material can be reduced as the insulation is exposed to moisture. Metal or wooden building structural materials, such as framing and beams, can degrade or corrode over and need to be replaced. Prolonged exposure to standing water also allows mold to grow on building structures or storage containers, which can damage the structures and substances contained therein, as well as pose a health risk.

SUMMARY OF THE INVENTION

The invention includes an insulated pipe including an elongated tube comprising a first end, a second end, and a sidewall extending therebetween; an insulating member at least partially enclosing a portion of the pipe sidewall, the insulating member comprising at least one channel extending through at least a portion of the insulating member. The insulated pipe also includes at least one coaxial moisture sensor positioned within at least a portion of the channel configured to sense moisture in the channel. The at least one coaxial moisture sensor includes: a dielectric member comprising a sleeve defining a center hole formed from an absorbent dielectric polymer material; an outer electrode electrically connected with an outer surface of the dielectric member, the outer electrode comprising a moisture permeable sleeve which permits moisture to pass to the dielectric member; and an inner electrode comprising a wire extending through the center hole of and electrically connected with an inner surface of the dielectric member. The dielectric member is in electrical contact with the first and second electrodes and maintains the first and the second electrodes spaced from one another.

The invention also includes a container configured to enclose objects in a low moisture environment. The container includes: a top portion, a bottom portion, and sides extending between the top portion and the bottom portion thereof. The container further includes at least one coaxial moisture sensor enclosed within a cavity defined by the top portion, bottom portion, and sides. The at least one coaxial moisture sensor comprising: a dielectric member comprising a sleeve defining a center hole formed from an absorbent dielectric polymer material; an outer electrode electrically connected with an outer surface of the dielectric member, comprising a porous sleeve for permitting moisture to pass through the sleeve; and an inner electrode comprising a wire extending through the center hole of and electrically connected with an inner surface of the dielectric member. The dielectric member is in electrical contact with the first and second electrodes and maintains the first and the second electrodes spaced from one another.

The invention also includes a method for detecting moisture in insulation surrounding a pipe including: applying an alternating electrical current to a coaxial moisture sensor positioned within a channel extending through insulation at least partially surrounding a pipe. The coaxial moisture sensor comprises: a dielectric member comprising a sleeve defining a center hole formed from an absorbent polymer material, a first electrode surrounding at least a portion of the dielectric member, and a second electrode extending through a portion of the center hole of the dielectric member. The method further includes continually or periodically measuring a complex impedance of the dielectric polymer material with sensor electronics connected to the first and/or the second electrodes and determining an amount of moisture within the insulation based on the measured complex impedance.

BRIEF DESCRIPTION OF THE DRAWINGS

These and other features and characteristics of the present disclosure, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limit of the invention.

Further features and other examples and advantages will become apparent from the following detailed description made with reference to the drawings in which.

DETAILED DESCRIPTION OF THE INVENTION

Figure 1A:
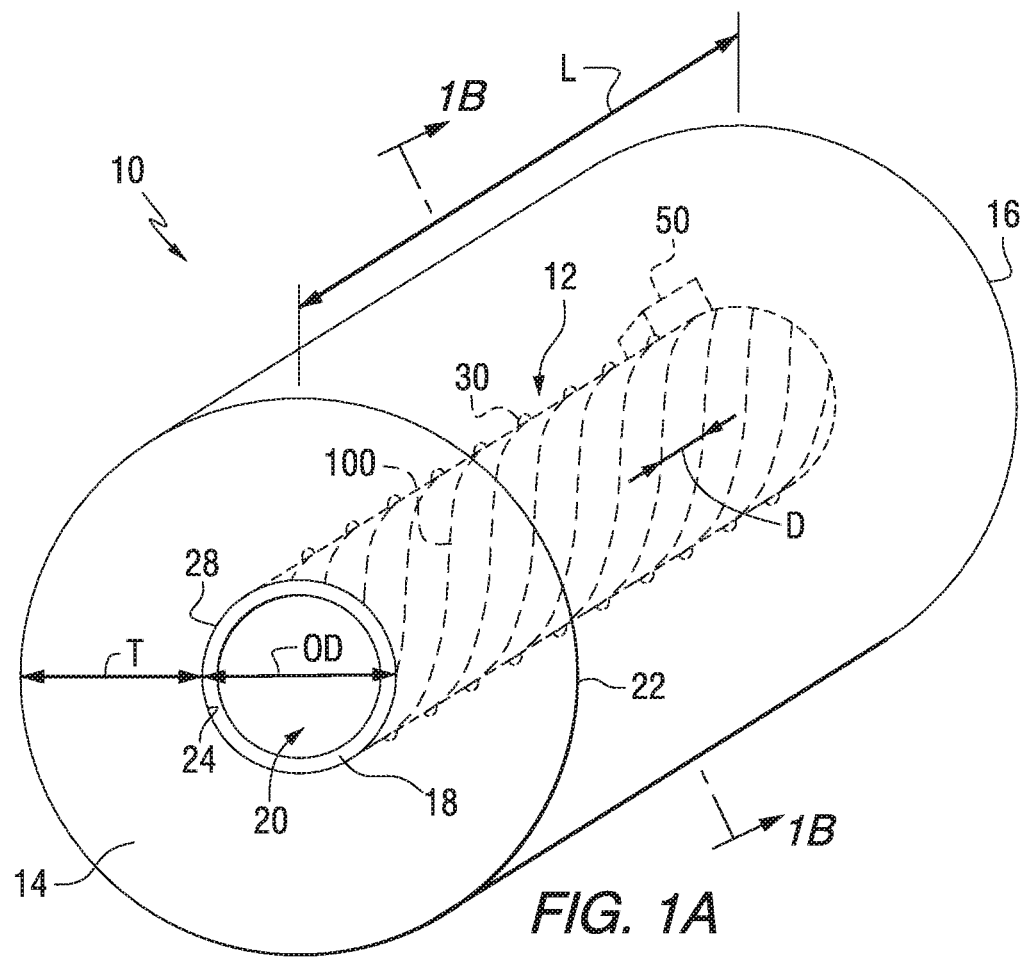
FIG. 1A is a perspective view of an insulated pipe including a coaxial moisture sensor according to an embodiment of the present disclosure.

For purposes of the following detailed description, it is to be understood that the invention may assume various alternative variations and step sequences, except where expressly specified to the contrary. Moreover, other than in any operating examples, or where otherwise indicated, all numbers expressing, for example, a duration of an electric pulse or of a pause between pulses, as used in the specification and claims are to be understood as being modified in all instances by the term "about". Accordingly, unless indicated to the contrary, the numerical parameters set forth in the following specification and attached claims are approximations that may vary depending upon the desired properties to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

Also, it should be understood that any numerical range recited herein is intended to include all sub-ranges subsumed therein. For example, a range of "1 to 10" is intended to include any and all sub-ranges between and including the recited minimum value of 1 and the recited maximum value of 10, that is, all sub-ranges beginning with a minimum value equal to or greater than 1 and ending with a maximum value equal to or less than 10, and all sub-ranges in between, e.g., 1 to 6.3, or 5.5 to 10, or 2.7 to 6.1.

As used herein, the singular form of "a", "an", and "the" include plural referents unless the context clearly dictates otherwise.

As used herein, the terms "right", "left", "top", "bottom", and derivatives thereof shall relate to the invention as it is oriented in the drawing figures. However, it is to be understood that the invention can assume various alternative orientations and, accordingly, such terms are not to be considered as limiting. Also, it is to be understood that the invention can assume various alternative variations and stage sequences, except where expressly specified to the contrary. It is also to be understood that the specific devices and processes illustrated in the attached drawings, and described in the following specification, are examples. Hence, specific dimensions and other physical characteristics related to the embodiments disclosed herein are not to be considered as limiting.

As used herein, the terms "communication" and "communicate" refer to the receipt or transfer of one or more signals, messages, commands, or other type of data. "Electrical communication" refers to receipt or transfer of power (e.g., current and/or voltage) between devices. For one unit or component to be in communication with another unit or component means that the one unit or component is able to directly or indirectly receive data or power from and/or transmit data or power to the other unit or component. This can refer to a direct or indirect connection that can be wired and/or wireless in nature. Additionally, two units or components can be in communication with each other even though the data transmitted can be modified, processed, routed, and the like, between the first and second unit or component. For example, a first unit can be in communication with a second unit even though the first unit passively receives data, and does not actively transmit data to the second unit. As another example, a first unit can be in communication with a second unit if an intermediary unit processes data from one unit and transmits processed data to the second unit. It will be appreciated that numerous other arrangements are also possible.

With reference to the figures, the present disclosure is generally directed to structures, such as building fixtures, vehicles, electronic devices, containers, and storage tanks enclosing, encapsulating, or including portions or areas which are intended to remain free from, or substantially free from, moisture and/or standing water. In some cases, moisture can damage these structures, as is the case with building fixtures (e.g., pipes and insulation) and vehicles. In other cases, the moisture could damage items contained within or enclosed by the structure, as is the case for a storage container or housing for an electrical device or appliance.

Figure 3:
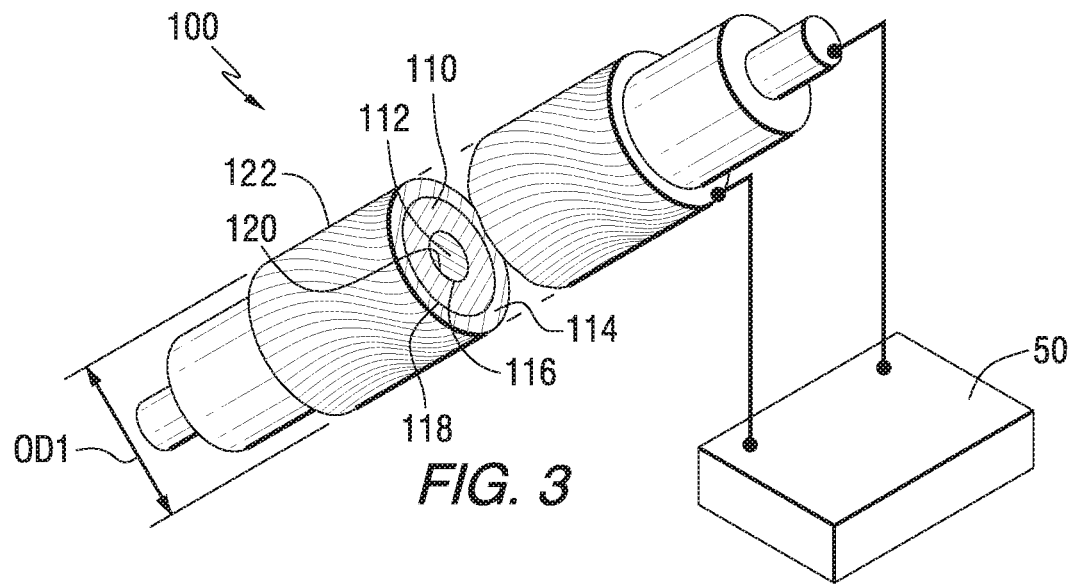
FIG. 3 is a perspective segmented view of a portion of a coaxial moisture sensor according to an embodiment of the disclosure.
Figure 4:
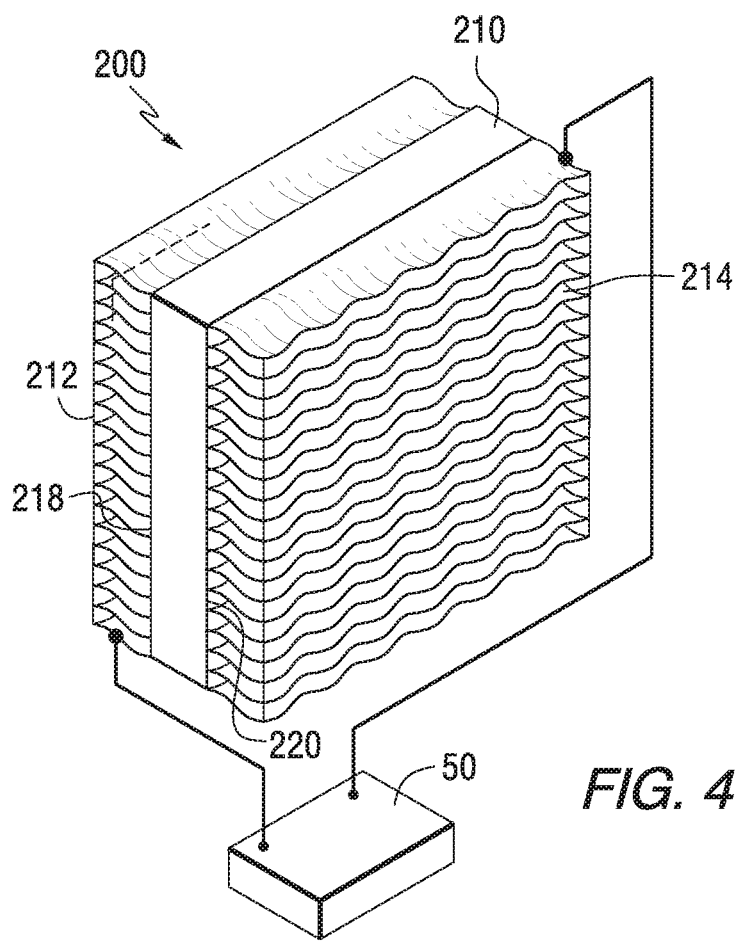
FIG. 4 is a perspective view of another embodiment of a moisture sensor.
Figure 5:
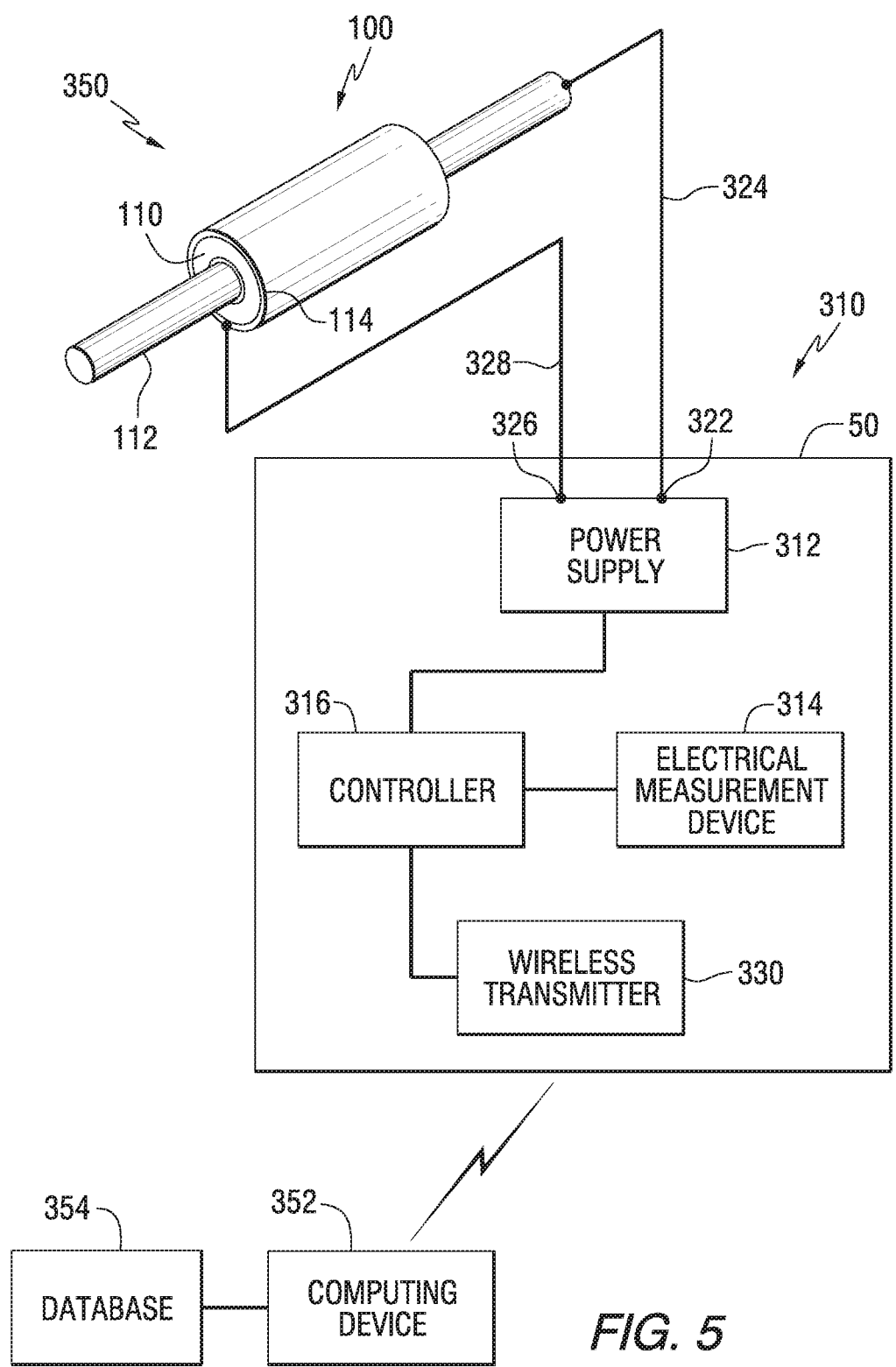
FIG. 5 is a schematic drawing of electronic circuitry of a moisture sensor according to an embodiment of the disclosure.

With specific reference to FIGS. 3-5, in order to identify, detect, or sense moisture and/or standing water in such structures, the structures disclosed herein include, are embedded with, and/or contain moisture sensors 100, 200 and associated electrical circuitry or sensor electronics 310, such as a power source 312, voltmeter or similar electrical measurement device 314, and controller 316. The moisture sensors 100, 200 and sensor electronics 310 are configured to detect moisture or standing water in proximity to the sensors 100, 200. In some examples, electrical signals from the moisture sensors 100, 200 may also detect a percentage of humidity in proximity to the moisture sensor 100, 200. For example, humidity could be measured to monitor performance of appliances intended to remain moisture-free, such as a paint booth or cure oven.

The moisture sensors 100, 200 disclosed herein include an absorbent moisture reactive and/or moisture sensitive portion, such as a sleeve 110 or layer 210, formed from a dielectric material. A dielectric material or dielectric is an electrical insulator that can be polarized by an applied electric field. When a dielectric is placed in an electric field, electric charges do not flow through the material, as they do in a conductor. Instead, the electric charges only slightly shift from their average equilibrium positions causing dielectric polarization. Because of dielectric polarization, positive charges are displaced toward the field and negative charges shift in the opposite direction. This phenomena creates an internal electric field that reduces the overall field within the dielectric itself. If a dielectric is composed of weakly bonded molecules, those molecules not only become polarized, but also reorient so that their symmetry axes align to the field.

The moisture sensors 100, 200 disclosed herein are configured to function as impedance moisture sensors, in which electrical impedance, i.e., the capacitance, resistance and complex impedance, of the dielectric material is monitored. Specifically, changes in electrical properties of the dielectric material corresponds to an amount of moisture absorbed by the dielectric material and/or a humidity level in proximity to the dielectric material. It has been determined that moisture permeation into the dielectric material primarily causes an increase in the capacitive component or complex impedance of the dielectric material of the moisture sensor 100, 200. In use, once moisture begins to enter into a structure or container, the absorbent moisture sensitive layer absorbs moisture, which causes electrical properties of the dielectric material to change. Specifically, complex impedance of the dielectric material increases as moisture is absorbed. The change is identified and used to calculate the moisture level.

For purposes of clarity, impedance is the measurement of the opposition to current flow in a circuit. For direct current (DC), the only opposition is the resistance of the circuit. For alternating current (AC), the current is opposed by the inductance and capacitance, as well as by the resistance. The combination of inductance and capacitance is referred to as reactance and makes up the complex component of impedance, while resistance forms the real component. Quantitatively, impedance is defined as the complex ratio of the voltage to the current at a given frequency. For a sinusoidal input, the polar form of the complex impedance relates the amplitude and phase of the voltage and current. The magnitude of the polar impedance is the voltage to current amplitude ratio. The phase of the polar impedance is the phase shift between the current and voltage.

According to another aspect of the disclosure, measurements from the moisture sensors 100, 200 can be used not only to determine an instantaneous water ingression rate into a structure or container, but also to record a history of the moisture ingression for the structure over a period of time. For example, impedance measurements from moisture sensors 100, 200 can be collected continually or periodically to identify a rate of moisture ingression at particular intervals. Evidence of moisture ingression over time may be used to identify times of day when moisture ingression commonly occurs or to determine if an amount of standing water in proximity to a moisture sensor increases or decreases over time. Such moisture ingression information may be used to help determine a cause of moisture entering the structure or container and/or to determine how to stop moisture from collecting in the structure or container.

Insulated Pipes with Moisture Sensors

Referring to FIGS. 1A-2B, the structure being monitored may be an insulated pipe 10 having at least one moisture sensor, such as the coaxial moisture sensor 100, for monitoring moisture in proximity to the pipe 10. As described in greater detail in connection with FIG. 3, the coaxial moisture sensor 100 is an impedance moisture sensor including a dielectric member or sleeve 110 enclosed between an inner electrode 112, which can be a conductive wire, and a permeable annular outer electrode 114. In some examples, the insulated pipe 10 could also include one or more planar moisture sensors 200, such as the planar moisture sensors shown in FIG. 4. The insulated pipe 10 includes an elongated tube 12 having a first end 14, a second end 16, and a sidewall 18 extending therebetween. The elongated tube 12 can be formed from any suitable material commonly used in the building industry including, for example, metal (e.g., copper or galvanized steel), ceramic, or plastic, such as, polyvinyl chloride (PVC). In many configurations, the tube 12 includes a hollow cylindrical member with a cylindrical sidewall 18 and defining a cylindrical cavity 20 extending axially therethrough. In other examples, the tube 12 and/or cavity 20 can have other cross sectional shapes including, but not limited to, a square, a rectangle, an oval, or combinations thereof. For example, a pipe 10 having a square shaped cross section could define a circular cavity. Dimensions of the tube 12 are largely dependent on intended use. For example, water supply pipes used for residential buildings may have an outer diameter OD of from 0.5 inch to 1.5 inches. PVC pipes used for plumbing often have an outer diameter from 0.75 inch to 3.0 inches.

The pipe 10 also includes an insulating member 22 at least partially enclosing a portion of the pipe sidewall. As shown in FIGS. 1A-2B, the insulating member 22 is an elongated structure including a central opening sized to receive the elongated tube 12, such that an inner surface 24 of the insulating member 22 is in contact with at least a portion of an outer surface 28 of the sidewall 18 of the elongated tube 12. A radial thickness T of the insulating member 22 is selected based on criteria including space considerations, material composition of the insulating material, and typical or expected environmental conditions surrounding the pipe 10. For example, pipes in interior walls of a building may only have a small amount of insulation. Pipes extending through exterior walls often require thicker insulation. In most cases, the thickness T of the insulating member can be between 0.5 inch and 2.0 inches. The insulating member 22 can be formed from any suitable insulating material as is used in the building industry, including, for example, fiber glass insulation, organic fiber materials (e.g., wool, cotton, or cellulose batts), spray foam materials (e.g., closed cell foams, isocyanate foams), and similar materials. In one example, the insulating member 22 is formed from FIBERGLAS™ pipe insulation manufactured by Owens Corning Insulating Systems, LLC of Toledo, Ohio. In some examples, the insulating member 22 can be covered by an outer wrap or jacket (not shown) formed from a polymer film, fiberglass mat, or aluminum foil.

The insulating member 22 also includes one or more channels 30 extending through at least a portion of the insulating member 22 sized to receive moisture sensors 100, 200. For example, for a coaxial moisture sensor 100 including an inner electrode formed on a wire 112 (shown in FIG. 3), the wire 112 can be positioned to extend through a channel 30 extending axially along a length L of the pipe 10. The channels 30 can be formed by any suitable method. For example, for spray foam insulation, foam may be sprayed around the tube 12 and moisture sensor(s) 100 and allowed to harden, thereby forming channels 30. In other examples, channels 30 could be cut or drilled into a surface or interior of insulating material and the moisture sensors 100, 200 could be fed through the channels 30.

As will be appreciated by those of skill in the art, the channels 30 can be positioned on or around the pipe 10 in a variety of configurations and arrangements within the scope of the present disclosure. Positioning of the channels 30 is generally determined based on structural properties of the pipe 10, size of the pipe 10, and, for example, what type of moisture is being detected. For example, as shown in FIGS. 1A-2B, the channels 30 can be formed on the inner surface 24 of the insulating member 22, so that the moisture sensors 100 are positioned between the tube 12 and the insulating member 22. In this position, moisture sensors 100 may be configured to detect when moisture has fully absorbed through the insulating member 22 and is nearly in contact with the elongated tube 12, which could cause corrosion or other structural damage. Moisture sensors 100, 200 positioned on the outer surface 28 of the elongated tube 12 may also be used to detect leaks from the tube 12, which could damage or degrade the insulating member 22. In other examples, channels 30 could be formed extending through an interior of the insulating member 22 to detect moisture collecting in the insulating member 22. For example, a channel 30 may extend between inner and outer surfaces of the insulating member 22. In this position, information from moisture sensors 100, 200 could be used to determine a moisture absorption depth into the insulating member 22 or, for example, how close moisture absorbed by the insulating member 22 is to contacting the elongated tube 12.

Figure 1B:
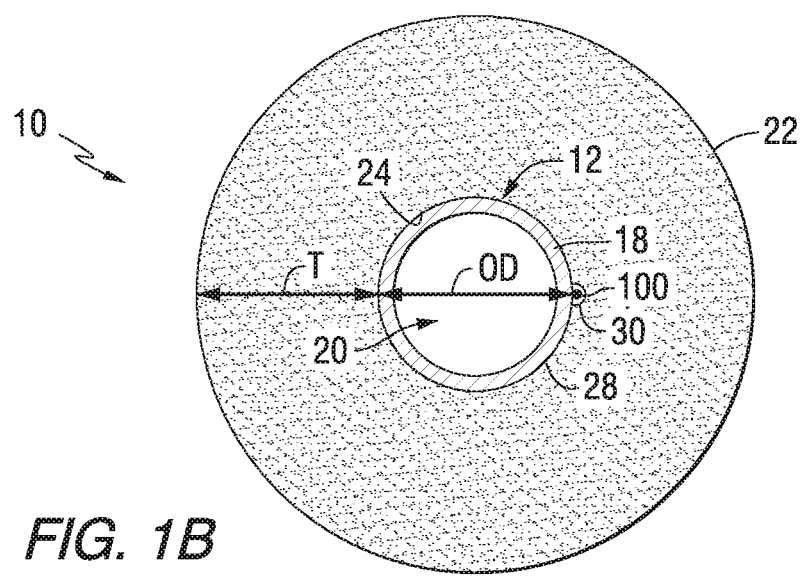
FIG. 1B is a cross-sectional view of the insulated pipe of FIG. 1A taken along line 1B-1B.

In one example, as shown in FIGS. 1A and 1B, the coaxial moisture sensor 100 is wrapped around the elongated tube 12 in a helical arrangement. The dimensions of the helix, such as a step distance D, can be selected based on criteria including the length of the moisture sensor 100, 200, length of the pipe 10 or elongated tube 12, or, for example, selected to cover regions of the pipe 10 most likely to be exposed to moisture. For example, leaks may be most likely to occur at joints between separate segments of the elongated tube 12. Accordingly, the moisture sensors 100 may be concentrated near such joints. In some examples, the moisture sensor 100 is capable of sensing moisture along its entire length. In that case, a moisture sensitive layer, such as a dielectric sleeve 110, extends along an entire length of the inner electrode 112 or wire. In other examples, separate dielectric sleeves 110 can be spaced apart along a length of the inner electrode 112 or wire at random or discrete intervals, such as every 2 inches, 5 inches, or 10 inches. Measurements from the separate dielectric sleeves 110 can be used to identify which portions of the pipe 10 have been exposed to moisture.

In some examples, the insulated pipe 10 includes multiple coaxial moisture sensors formed on different wires. For example, coaxial moisture sensors 100 can be configured to form a double helix extending axially along the elongated tube 12, thereby increasing the surface area of the pipe 10 and/or tube 12 being monitored for moisture. Dimensions of the moisture sensors are not limiting for the invention; however, in order to fit within the channels 30, the moisture sensor 100 can be manufactured to be as thin as possible. For example, coaxial moisture sensors formed as described herein can be manufactured with a maximum outer diameter OD1 (shown in FIG. 3) of 0.060 inch or less.

With continued reference to FIG. 1A, the moisture sensor 100 is connected to a control box 50 mounted to the outer surface 28 of the sidewall 18 of the elongated tube 12. As described in connection with FIG. 5, the control box 50 includes electronic circuitry configured to receive electrical signals from the moisture sensor(s) 100 and process the received signals to calculate a complex impedance of the moisture sensitive layer or dielectric sleeve 110, as described in greater detail herein.

Figure 2A:
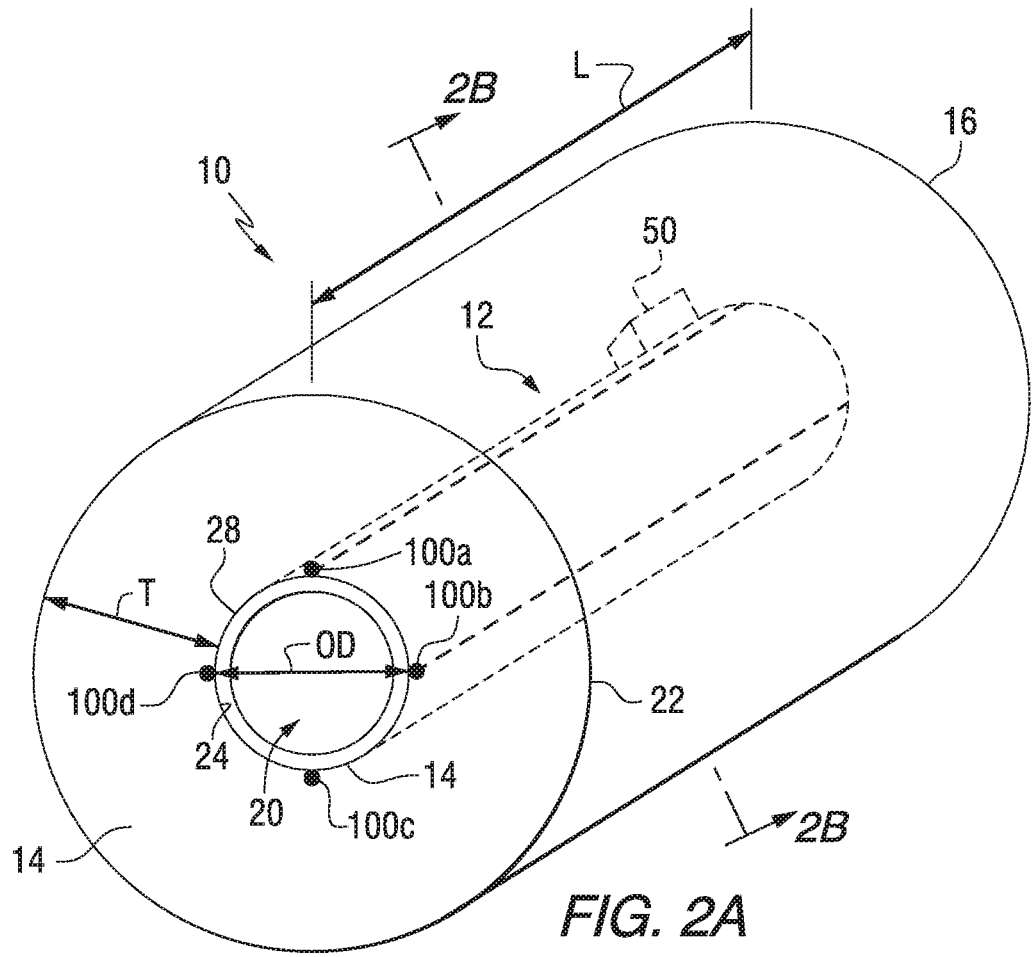
FIG. 2A is a perspective view of another embodiment of an insulated pipe including a coaxial moisture sensor.
Figure 2B:
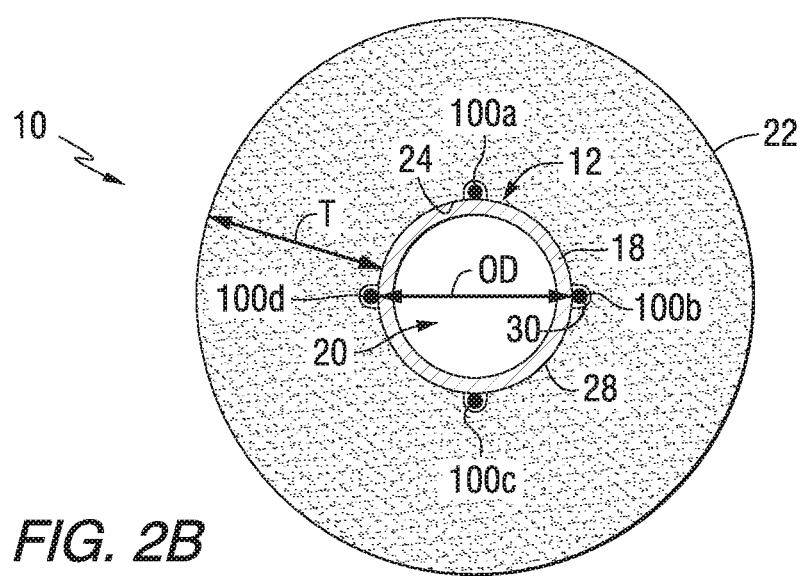
FIG. 2B is a cross sectional view of the insulated pipe of FIG. 2A taken along line 2B-2B.

As shown in FIGS. 2A and 2B, a pipe 10 may include a number of substantially straight coaxial moisture sensors extending axially along the sidewall of the tube 12. For example, the insulated pipe 10 can include a first coaxial moisture sensor 100a extending axially along the outer surface of the pipe at 12:00 (0 degrees), a second moisture sensor 100b extending axially at 3:00 (90 degrees), a third moisture sensor 100c at 6:00 (180 degrees), and a fourth moisture sensor 100d at 9:00 (270 degrees). The pipe 10 also includes a control box 50 electrically connected to the moisture sensor(s) 100a, 100b, 100c, 100d. As described above, the control box 50 includes electrical circuitry for receiving and processing electrical signals from the moisture sensors 100a, 100b, 100c, 100d.

Dielectric Moisture Sensors

With reference to FIG. 3, the coaxial moisture sensor 100 of the pipe 10 includes the moisture sensitive layer, such as the dielectric sleeve 110 defining a center hole 116, the inner electrode 112, and outer electrode 114. The moisture sensor 100 may also include an outer protective layer 122, such as an outer jacket or sleeve. The protective layer 122 can be formed from the same material as the dielectric sleeve 110. While the protective layer 122 is not necessary to function of the sensor 100, the protective layer 122 is believed to improve electrical efficiency and accuracy of the sensor 100.

The dielectric sleeve 110 and other portions of the moisture sensor 100 may be made from materials that are non-reactive with materials of other portions of the pipe 10, such as the insulating member 22 and elongated tube 12. The dielectric sleeve 110 can be formed from any insulating material having dielectric properties. The dielectric material may be an absorbent polymer material, such as one or more of nylon of any chain length (e.g., nylon 4-6, nylon 6, nylon 6-6, nylon 6-12, nylon 11), polyamide-imide, polybenzimidazole, polyethersulfone, or polysulfone. Since the coaxial moisture sensor 100 is formed over the inner electrode 112 or wire, the dielectric material may be selected for compatibility with wire manufacturing and may have a large saturated moisture capacity (e.g., an equilibrium water absorption of 1.5% or more at ordinary atmospheric conditions) and a melting temperature greater than a laminate processing temperature for other portions of the moisture sensor 100. For example, at ordinary atmospheric conditions (23° C./60% relative humidity) equilibrium water absorption is 3.5% for nylon 6, 2.5% for nylon 6-6. The melting temperature of nylon 6 is about 215° C. and the melting temperature of nylon 6-6 is about 264° C.

The moisture sensor 100 further includes the opposing electrodes, such as the outer electrode 114, which is electrically connected with an outer surface 118 of the dielectric sleeve 110, and the inner electrode 112 or wire, which extends through the center hole 116 of and is electrically connected with an inner surface 120 of the sleeve 110. For example, the outer electrode 114 can be in surface contact with the outer surface 118 of the dielectric sleeve 110 and the inner electrode 112 can be in surface contact the inner surface 120 of the sleeve 110.

The inner electrode 112 and the outer electrode 114 may be formed from an electrically conductive material having a constant electrical conductivity over time at a fixed temperature. For example, the electrodes 112, 114 can be formed from one or more of the noble metals (e.g., ruthenium, rhodium, palladium, silver, osmium, iridium, platinum, and gold) or non-noble metals and alloys such as, but not limited to, copper, tin-plated copper, nickel-plated copper, nickel-chromium, aluminum, and combinations thereof. Since the outer electrode 114 surrounds the dielectric member or sleeve 110, the outer electrode 114 may be at least partially porous, so that moisture or water passes through the outer electrode 114 and is absorbed by the dielectric member or sleeve 110. For example, the outer electrode 114 can be a mesh material formed from woven metal fibers or filaments. The outer electrode 114 can also comprise a carbon mesh or a flexible metal sheet comprising holes or openings for permitting water to pass therethrough.

The dielectric member or sleeve 110 may be in electrical contact with the inner and outer electrodes 112, 114 and maintains the inner and the outer electrodes 112, 114 spaced apart from one another. For example, the sleeve 110 maintain the inner and outer electrodes 112, 114 out of surface contact with one another. The inner electrode 112 and the outer electrode 114 may be made of the same material to avoid chemical reaction between two different metals. The moisture sensor 100 may further comprises any number of additional moisture permeable conducting or insulating layers, which do not substantially change the electrical response of the moisture sensor 100, but may be useful for fabrication or installation of the sensor 110. For example, any additional moisture permeable conducting or insulating layers should not affect the complex impedance of the dielectric sleeve 110, should not create a separate path between the electrodes 112, 114 for current to flow through having a lower resistance than the sleeve 110, and should not reduce a potential of an electrical signal applied between the electrodes 112, 114 through the dielectric sleeve 110.

In one specific example of the coaxial moisture sensor 100, the inner electrode 112 is formed from a solid or stranded tin plated copper wire, such as a 44 American wire gauge (AWG) tin-plated copper wire with a 75% braid coverage, and the outer electrode 114 is made of a tin plated copper mesh to provide passageways for moisture to move through the outer electrodes to contact the dielectric material.

In another specific example of the coaxial moisture sensor 100, the inner electrode 112 is formed from 28 AWG 7/36 tin-plated stranded copper wire. The dielectric member or sleeve 110 is made of nylon-6 purchased from Honeywell and sold under the trademark AEGIS® H55WC nylon jacket compound, which is extruded over the inner electrode 112 to a nominal wall thickness of 0.005 inch. The outer electrode 114 is made of 44 AWG tin plated copper braid, braided over the dielectric sleeve, with a nominal 75% coverage. An outer insulating layer or protective layer 122 is formed from AEGIS® H55WC nylon jacket compound extruded over the braid to a nominal outside diameter of 0.045 inch.

With reference to FIG. 4, an embodiment of a planar moisture sensor 200 configured to detect changes in complex impedance of a moisture sensitive layer comprising a dielectric material is illustrated. The planar moisture sensor 200 comprises a first conductive electrode 212 spaced apart from a second electrical conductive electrode 214. The conductive electrodes 212, 214 are porous structures, such as perforated metal plates, meshes, carbon mesh, or similar structures as are known in the art. The conductive electrodes 212, 214 can be formed from any of the noble and non-noble metal materials described above. As discussed previously, the electrodes 212, 214 are generally formed from the same metal material to avoid chemical reactions between different metals. The planar moisture sensor 200 further comprises a dielectric layer 210 positioned between and in physical contact, or close proximity, with the first electrode 212 and the second electrode 214. The dielectric layer 210 can be an extruded film layer formed from an absorbent polymer material, such as one or more of nylon of any chain length (e.g., nylon 4-6, nylon 6, nylon 6-6, nylon 6-12, nylon 11), polyamide-imide, polybenzimidazole, polyethersulfone, or polysulfone, as described above.

In a specific example of the planar moisture sensor 200, the moisture sensor 200 comprises a dielectric layer 210 formed from a layer of nylon-6 dielectric material, ranging in thicknesses from 0.001 inch to 0.032 inch, and having a width of 0.5 inch. A length of the dielectric material can vary depending on a size of an area to be monitored by the sensor 200. In a specific example, the electrodes 212, 214 of the planar moisture sensor 200 are made of nickel plated copper metalized polyester fabric tape, with conductive pressure sensitive acrylic adhesive. The electrodes 212, 214 generally are the same length and width as the dielectric member or layer 210. The electrodes 212, 214 can have a nominal thickness of 0.001 inch to 0.005 inch (0.025 mm to 0.13 mm) or 0.002 inch to 0.004 inch (0.05 mm to 0.1 mm). The electrodes 212, 214 can be from 0.25 inch to 0.5 inch wide. In some examples, the electrodes 212, 214 of the planar moisture sensor 200 are joined to the top surface 218 and the bottom surface 220 of the dielectric material by conductive pressure sensitive acrylic adhesive.

Moisture Sensor Electronics and Monitoring System

A schematic drawing showing a monitoring system 350 for analyzing and reporting such information to a user is provided in FIG. 5. The moisture monitoring system 350 includes one or more moisture sensors, such as a coaxial moisture sensor 100, sensor electronics 310 configured to receive and process electrical signals from the moisture sensor 100, and feedback or data collection devices in wired or wireless communication with the sensor electronics 310. As described above, some components of the electrical circuitry or sensor electronics 310 can be contained in a control box, such as a control box 50 mounted to a portion of the insulted pipe 10 (shown in FIGS. 1A-2B). Components of the monitoring system 350, such as a building monitor device, alarm systems, feedback devices, and similar electronic components, can be remote from and in wired or wireless electrical communication with the sensor electronics 310 contained in the control box 50.

Figure 6:
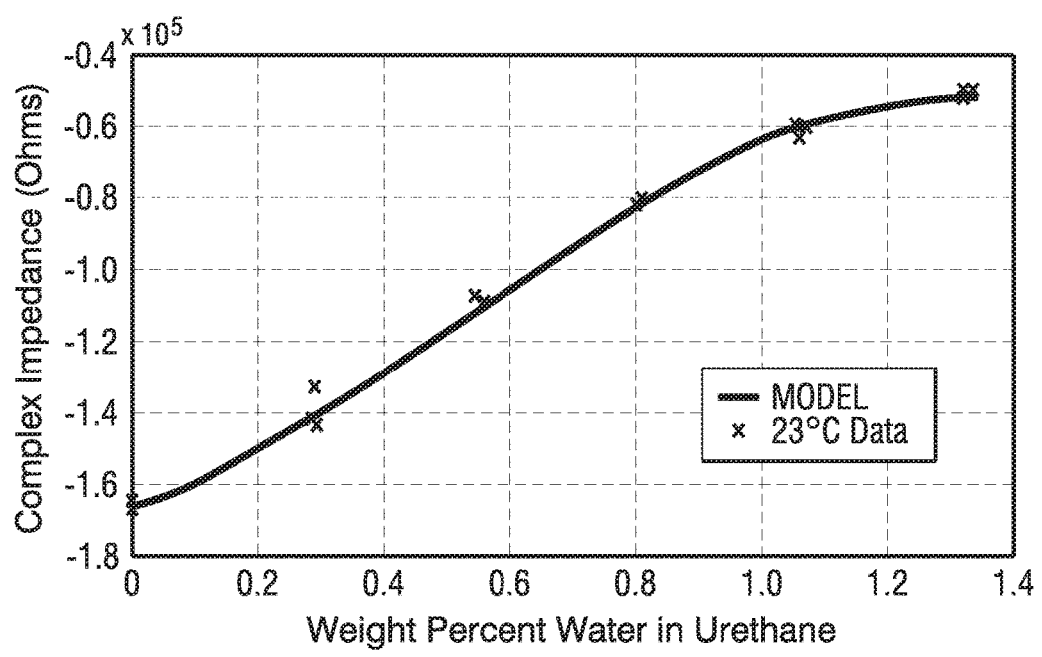
FIG. 6 is a graph showing changes in complex impedance (ohms) as a function of moisture content in wt. % for a dielectric material according to an aspect of the disclosure.

The sensor electronics 310 are configured to monitor, detect, or identify changes in complex impedance of the dielectric material of the moisture sensor 100. The sensor electronics 310 can also be configured to calculate moisture content of the dielectric material and/or a moisture content of structures surrounding the moisture sensor 100 based on the measured complex impedance. In particular, as will be appreciated by those skilled in the art, a measured general or complex impedance of the moisture sensor 100 can be calibrated to determine a moisture content of the moisture sensitive layer and to determine a moisture content of structures surrounding the sensor through a suitable model and/or calibration curve. A non-limiting embodiment of a calibration curve, which can be used with the moisture sensor disclosed herein, is shown in FIG. 6.

With specific reference to FIG. 5, the sensor electronics 310 in electrical communication with the moisture sensor 100 include a power supply 312, such as an AC power supply, an electrical measurement device 314, and a controller 316, such as a computer processor, configured to receive an electrical signal from the moisture sensor 100 and calculate a complex impedance and moisture content based on the received signal. In some examples, the electrical power supply 312, the electrical measurement device 314, and the controller 316 are combined in a single unit or instrument, e.g. a console of the type shown in FIG. 18A of, and disclosed in U.S. Pat. No. 8,155,816. In other examples, the power supply 312, measurement device 314, and controller 316 are separated units in wired or wireless communication with one another and with the moisture sensor 100.

The sensor electronics 310 also include elements for operatively connecting the electrodes 112, 114 of the moisture sensor 100 to the control box 50 and sensor electronics 310. For example, the inner electrode 112 of the moisture sensor 100 can be connected to a pole 322 of the power supply 312 through a wire or lead 324. The outer electrode 114 can be connected to a second pole 326 of the power supply 312 by a second wire or lead 328 to apply a voltage to the moisture sensor 100. This connection allows the moisture sensor 100 to act as an electrical circuit in which the electrical power supply 312 applies an electrical potential to the moisture sensor 310 through the leads 324, 328.

The power supply 312 can be any conventional electrical source, such as, but not limited to, a battery, an electrical generator, and the like for applying a voltage to the moisture sensor 310. The power supply 312 can be configured to apply alternating electrical current to the inner and outer electrodes according to a pattern or protocol, which can be directed by the controller 316.

The electrical measurement device 314 is configured to measure complex impedance (ohms) of the moisture sensor 310 based on an electrical signal received from the inner and outer electrodes 112, 114. For example, the electrical measurement device can be an ammeter or voltmeter operatively connected to the electrodes 112, 114. In other examples, complex impedance (ohm) output of the moisture sensor 100 can be measured using a variety of standard readout sensor circuits, e.g. of the type disclosed in U.S. Pat. No. 9,347,905.

The controller 316 can be any type of electronic or computerized device with sufficient processing capacity to analyze information provided by the electrical measurement device 314. For example, the controller 316 can be a dedicated electronic device installed in the control box 50. The controller 316 can also be a computer device with software for receiving and processing information from the electrical measurement device 314. The controller 316 can measure complex impedance from the sensor 310 by causing the power source 312 to provide a predetermined or specifically set electrical potential to the electrodes 112, 114 of the moisture sensor 100 and measuring a response from the moisture sensor 100 with the measurement device 314. The controller 316 can collect and/or calculate the electrical potential of the moisture sensor 100 via the electrical measurement device 314 to calculate complex impedance and/or moisture content of the dielectric material of the sensor 100.

An impedance measurement for the coaxial moisture sensor 100 can be performed by the following process. This process can also be used to calculate complex impedance for the planar moisture sensor 200, shown in FIG. 4. First, moisture penetrates through the insulation material of the pipe, eventually reaching and being absorbed by the dielectric material or sleeve 110 of the moisture sensor 100. An amount of moisture absorbed by the dielectric sleeve 110 is calculated based on the predictable increase in complex impedance (ohms) resulting from the absorbed moisture. In order to measure complex impedance, voltage is applied to the electrodes 112, 114 and the impedance of the circuit measured. As the dielectric material or sleeve 110 continues to absorb moisture, the dielectric material becomes saturated with moisture and no longer significantly absorbs moisture. The absolute moisture content of the dielectric material depends on the thickness and absorption coefficient of the dielectric material. The absolute moisture content of the dielectric material may also be temperature dependent. Accordingly, a calibration curve or model for moisture content of the sensor may be a temperature dependent model.

The impedance measurement may be made by analyzing a phase shift of a known frequency applied to the moisture sensor 100. In that case, the electrical power supply 312 applies an AC voltage to the moisture sensor 100, as set or specified by the controller 316. This applied voltage results in a measured potential on the sensor 100, which can be measured by the electrical measurement device 314. Importantly, the measured position is different in phase and magnitude from the voltage applied by the power supply 312. Since the electrical power supply 312 applies a set voltage and the electrical measurement device 314 reads or measures a voltage difference from the moisture sensor 100, the electrical measurement device 312 and/or the controller 316 are capable of calculating the complex impedance (ohms). Specifically, the complex impedance is calculated based on a voltage magnitude and a phase difference between the inner electrode 112 and outer electrode 114 of the moisture sensor 100. The complex impedance is then used to indicate the amount of moisture absorbed by the dielectric material or sleeve 110 of the moisture sensor 100. The electrical signal frequency used for this measurement is typically chosen to maximize the response of the sensing element to moisture change, however multiple frequencies can be used to improve accuracy and reduce the impact of noise.

In another example, the impedance measurement is made by applying a DC voltage across the electrodes 112, 114 and the charge time is measured (time it takes for the sensing element to reach the applied DC voltage). The electrical power supply 312 applies the DC voltage to the moisture sensor 100, again as set or specified by controller 316. This applied voltage results in a measured potential difference (as measured by the electrical measurement device 314) on sensor 100 that approaches the applied voltage. The electrical measurement device 314 or the controller 316 is able to calculate the capacitance (farads) of the moisture sensor 100 based on a time to reach the applied voltage. The capacitance of the sensor 100 is then used to indicate the amount of moisture absorbed by the dielectric material or sleeve 110 of the moisture sensor 100. In order to obtain continuous measurements, a changing DC voltage can be used, as well as measurement of both charge and/or discharge times.

Once complex impedance is calculated, the controller 316 is configured to determine an amount of moisture absorbed by the moisture sensitive layer or dielectric sleeve 110 based on the measured complex impedance. As described above, a graph or calibration curve comprising a measured complex impedance is illustrated. As shown in FIG. 6, the "y", or vertical axis, is the imaginary component of the complex impedance (ohms) and the "x", or horizontal axis, is the moisture content of a structure, such as the insulation member, which surrounds the moisture sensor 100. More specifically, the graph shown in FIG. 6 is a model (solid curve) with one set of recorded data for the complex impedance (ohms) of the sensor 100.

The monitoring system 350 also includes components which analyze data from the moisture sensors 100 and controller 316 and provide the information to a user. For example, information about moisture level or trends over time can be analyzed to identify when moisture levels increase or when leaks are mostly likely to occur. Such information can be displayed to a user on a remote computer device 352, such as a personal computer, tablet, smart phone, or similar device in wired or wireless communication with the controller 316 and moisture sensor 100. For example, the controller 316 can be coupled to a wired or wireless transmitter 330 for sending data from the controller 316 to a remote computer device 352 of the monitoring system 350.

The controller 316 and wireless transmitter 330 may be configured to send periodic updates or reports about measured moisture or complex impedance to the remote device 352. In that case, the monitoring system 350 can include computer memory, such as a database 354, for storing received information from the moisture sensor 100 and/or controller 316. For example, the database 354 may store moisture or complex impedance values over time to create a historical record documenting moisture ingress into a structure or container.

The computer device 352 can also display or provide real time alerts or notifications about elevated moisture levels to the user. In order to generate such alerts, the controller 316 can be configured to compare a measured complex impedance or moisture level measured by the moisture sensor 100 to a predetermined threshold value. The predetermined threshold value could correspond, for example, to an amount of moisture that the insulating member can absorb before damage to the insulated pipe or insulating material begins to occur. When the controller 316 determines that the measured moisture value exceeds the predetermined threshold value, an alert is generated to inform the user about the increased moisture. The alert or notification can be wirelessly transmitted from the controller 316 to the remote computer device 352. The remote computer device 352 can be configured to provide visual and/or audio indications to the user informing the user about the increased moisture levels.

In some examples, the remote device 352 can be configured to receive information from a plurality of moisture sensors 100 located at different positions on a structure or container being monitored. The controller 316 could also receive information from other moisture sensors or other types of sensors located on different structures or devices. By receiving and analyzing moisture measurements from different locations, it is possible to determine which areas of a structure or container receive the most moisture and/or are mostly likely to be damaged by moisture. Considering information from multiple sensors 100 also allows the user to evaluate whether certain sensors are functioning properly. For example, if different sensors located in similar areas of a structure or container detect different complex impedance or moisture values, it may indicate that a sensor is malfunctioning and should be repaired or replaced.

In a similar example, the computer device 352 could be a building-wide monitoring system that receives moisture measurements from moisture sensors positioned on different electrical devices, appliances, and/or building fixtures located throughout the building. The received moisture sensor information could be used to evaluate which building systems are functioning normally. In a similar manner, moisture measurements from different sensors could be compared to determine a source of moisture or to identify leaks that only affect some floors or areas of the building. In a similar manner, the computer device 352 could be a computer control system for a vehicle, such as an airplane or automobile. In that case, moisture measurements from different locations on the vehicle could be used to evaluate performance of different vehicle systems, determine which vehicle systems are functioning in an expected manner, and/or to schedule maintenance activities for different vehicle systems.

Electronic Housing Including Moisture Sensors

Figure 7A:
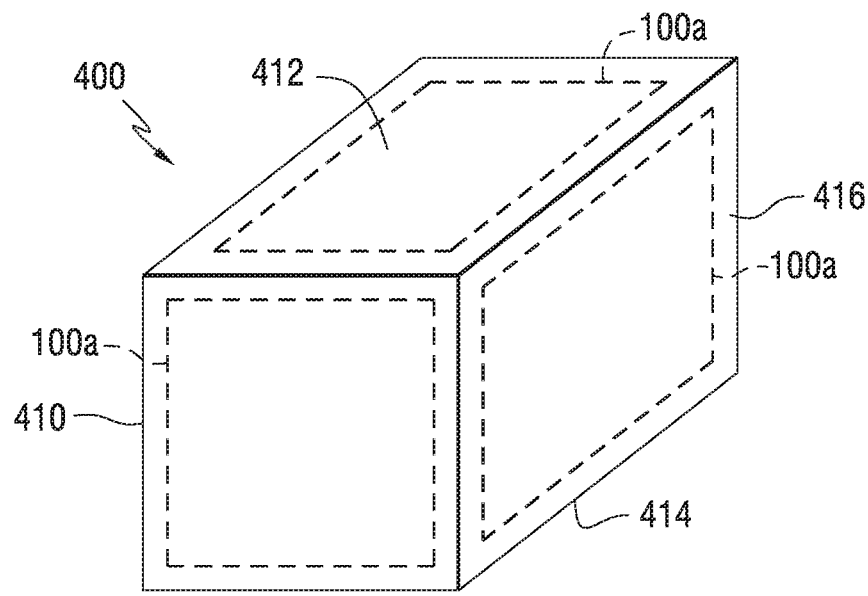
FIG. 7A is a perspective view of an electronic device including moisture sensor(s) for detecting moisture ingression through the device housing, according to an embodiment of the disclosure.
Figure 7B:
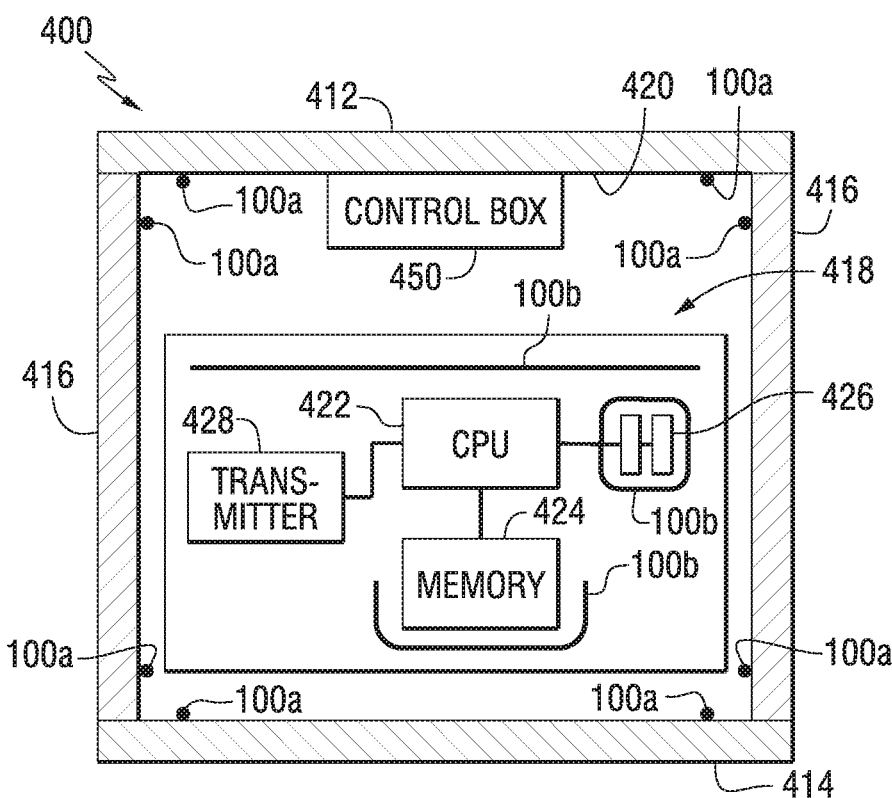
FIG. 7B is a schematic drawing of the electronic device of FIG. 7A.

According to another aspect of the disclosure, the coaxial moisture sensor 100 and monitoring system 350 disclosed herein can be used to monitor structural integrity of a housing or container and, in particular, to identify moisture ingression through the housing or container, which could damage goods or devices stored therein. For example, the container or housing could be a housing of an electronic device 400, such as a small appliance or portable electronic device (e.g., a tablet computer, cell phone, smartphone, personal digital assistant (PDA), calculator, or similar device), as shown in FIGS. 7A and 7B. In that case, the moisture sensor 100 could be configured to detect moisture ingress through the housing or container, which could damage electrical components contained therein.

In other examples, the container could be a container for perishable goods, such as food items, which would be damaged or destroyed when exposed to moisture. In that case, information about moisture ingress through the container may be used to determine when a container needs to be repaired or replaced, or when food items in the container have spoiled and should be discarded. In other examples, as described in greater detail in connection with FIGS. 8A, 8B, and 9, the container could be a liquid storage tank, such as a fuel storage tank. In that case, measurements from moisture sensors 100 could detect leaks from the tank, moisture ingress into the tank, a volume of liquid in the tank, and/or a concentration of liquids in the tank.

An exemplary electronic device 400 comprising coaxial moisture sensors 100a, 100b configured to identify moisture ingress into the device 400 is shown in FIGS. 7A and 7B. Moisture sensors 100a, 100b can be the impedance moisture sensors 100 formed on an inner electrode 114 or wire, as shown in FIG. 3. The electronic device 400 includes a housing 410 comprising a top 412, a bottom 414, and sides 416 extending therebetween. The housing 410 encloses an interior volume or cavity 418 and prevents moisture ingression into the cavity 418. As such, the housing 410 is generally formed from a non-porous material, such as metal, plastic, or glass. In some examples, the housing 410 is an integral structure, such as a plastic structure formed by a molding process. In other examples, the housing 410 is formed from various segments or portions connected together to form the housing 410. In that case, joints between the segments or portions of the housing 410 may include adhesives, solder, or sealing materials to reinforce the joints and to prevent moisture from leaking into the housing 410 through the joints. The housing 410 could also include an opening or port covered by a removable cap or cover to allow a user to access the cavity 418 to, for example, manipulate electronic components contained in the cavity 418. In that case, the cover or port could include a seal to prevent moisture ingression between the cover and port.

As shown in FIG. 7B, the electronic device 400 also includes electronic components stored in the cavity 418. For example, the device 400 can include a processor or controller, such as a CPU 422, operatively connected to computer memory 424, and a wireless transmitter 428. The electronic device 400 can also include various other electronic components including, in the case of consumer appliances, motors, heating elements, and associated controllers. For portable electronic devices such as smart phones, the electronic device 400 can also include a visual display, a cellular transceiver, speakers, microphones, and similar components, as are known in the art. The electronic device 400 can also include power supply components, such as batteries 426, for providing power to the CPU 422 and other components.

As shown in FIGS. 7A and 7B, moisture sensors 100a are positioned in the cavity 418 and are configured to detect moisture ingress through portions of the housing 410. The moisture sensors 100a can be arranged in a variety of patterns based, for example, on which areas of the housing 410 are most likely to be exposed to moisture and/or which areas of the housing are most likely to leak. For example, moisture sensors 100a may be positioned near joints, corners, between adjacent segments or walls of the container 410, or near covered openings (e.g., a cover of a battery port of an electronic device), since moisture often enters the housing 410 through such areas or openings. As shown in FIGS. 7A and 7B, moisture sensors 100a are positioned around peripheral portions of the top 412 and sides 416 of the housing 410 for detecting moisture ingression between portions of the sides 416 and/or between the sides 416 and top 412 or bottom 414 of the housing 410.

Other moisture sensors can be positioned in the cavity 418 in proximity to important electrical components of the electronic device 400. For example, as shown in FIG. 7B, moisture sensors 100b are positioned near the CPU 422, computer memory 424, and batteries 426.

The electronic device 400 can also include a control box 450 containing electrical circuitry or sensor electronics for receiving and processing information from the moisture sensors 100a, 100b positioned in different portions of the cavity 418. As in previous examples, the control box 450 can enclose a power supply, electronic measurement device, and controller (shown in FIG. 5) in electronic communication with the moisture sensors 100a, 100b. The control box 450 can be provided in any convenient location in proximity to other portions of the housing 410. For example, as shown in FIG. 7B, the control box 450 is placed in the cavity 418 near the interior surface 420 of the top 412 of the housing 410. In other examples, the control box 450 could be mounted to a side 416 or top 412 of the housing 410. In other examples, the control box 450 could be remote from the container and in wired or wireless communication with the one or more moisture sensors 100a, 100b through suitable data transmission components, as are known in the art.

The moisture sensors 100a, 100b are configured to detect moisture ingression through the housing 410. Specifically, electrical signals from the moisture sensors 100a, 100b are processed by sensor electronics in the control box 450 to measure a complex impedance and/or detect moisture based on information sensed by the moisture sensors 100a, 100b. In some examples, the sensor electronics in the control box 450 can transmit warnings or notifications to remote devices when moisture is detected. In some examples, sensor electronics in the control box 450 can also communicate with the electronics, such as the CPU 422, of the electronic device 400 when moisture is detected. For example, in order to avoid or reduce damage caused from moisture ingression through the housing 410, the controller 316 (shown in FIG. 5) of the moisture sensors 100a, 100b can be configured to transmit a signal to the CPU 422. In response to the signal from the controller 316, the CPU 422 can be configured to perform actions to protect components of the electronic device 400 including causing electrical components of the device 400 to turn off or power down, causing the computer memory 424 to perform a save function to preserve data, or causing the wireless transmitter 428 to transmit data from the device 400 to a remote source, so that it can be stored safely in the event that moisture damages the device 400.

After a period of time, if the moisture sensor 100 detects that moisture level has dropped and that it is safe to continue operating the electronic device 400, the controller 316 of the moisture sensor 100 could provide an instruction to the CPU 422 of the electronic device 400 instructing the device 400 to resume normal operation.

Storage Tank with Moisture Sensors

According to another aspect of the disclosure, one or more coaxial moisture sensors 100a, 100b, 100c can be mounted to a liquid storage tank 500, such as a storage tank for storing liquid fuels, such as petroleum, gasoline, diesel, liquid propane, kerosene, and liquefied natural gas. In some examples, coaxial moisture sensor can be configured to monitor a volume of liquid in the tank 500. In other examples, moisture sensor(s) could be arranged to detect leaks from and/or moisture ingress into the tank 500. In other examples, measurements from the moisture sensors could be used to detect a concentration of polar and non-polar fluids in the tank. For example, measurements from moisture sensors could be used to detect a concentration of oil and water in a storage tank 500.

Figure 8A:
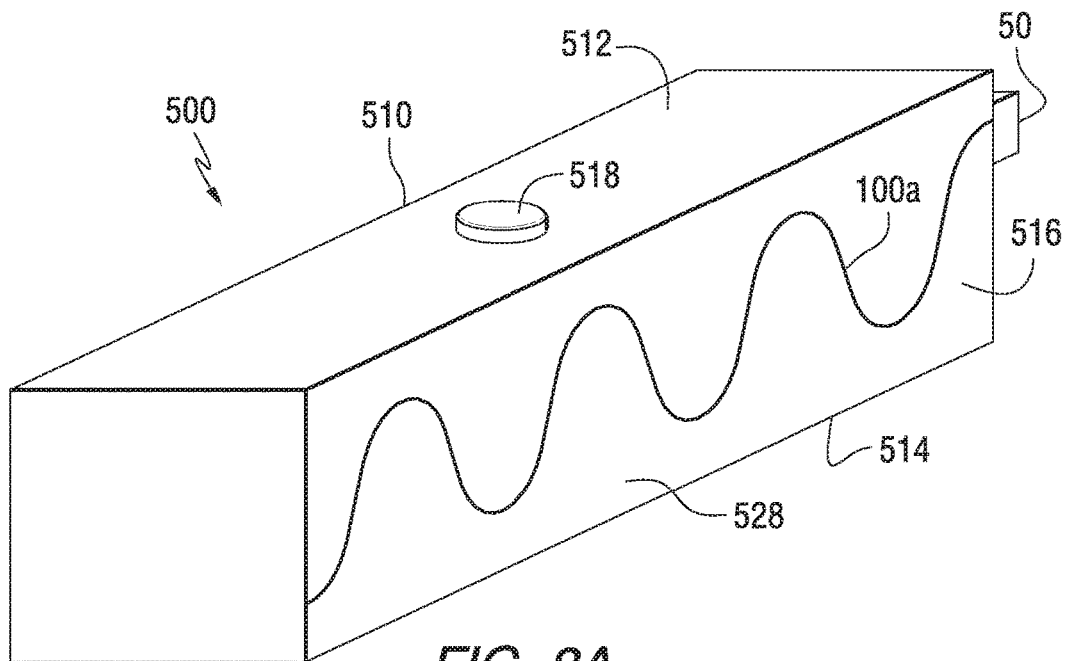
FIG. 8A is a perspective view of a storage tank including moisture sensor(s) for detecting moisture ingression into the tank and other information according to an embodiment of the disclosure.
Figure 8B:
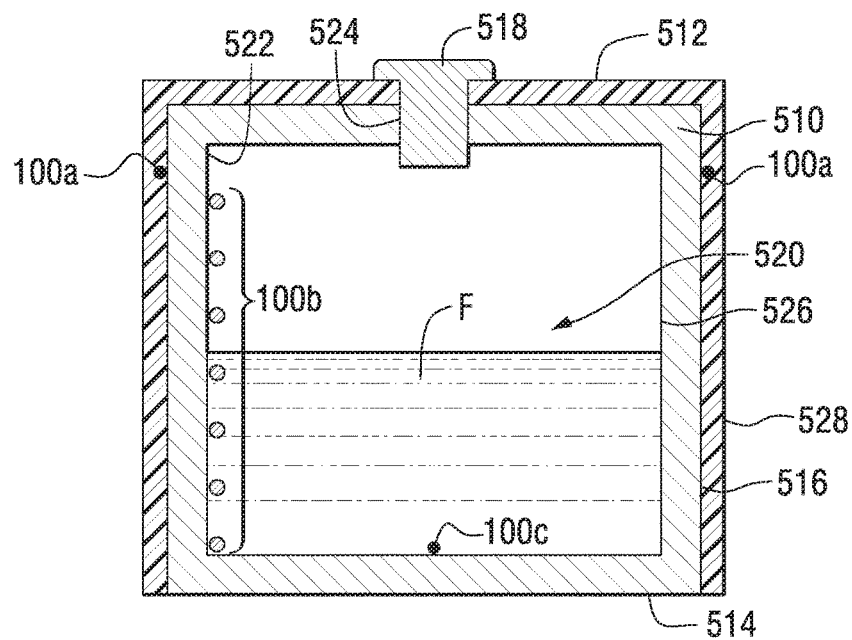
FIG. 8B is a cross sectional view of the storage tank of FIG. 8A taken along line 8B-8B.

With reference to FIGS. 8A and 8B, the storage tank 500 can comprise a body 510 having a top 512, a bottom 514, and sides 516 extending therebetween. The body 510 encloses an interior volume 520 or storage capacity for a liquid contained in the tank 500. The tank 500 can have a wide range of volumes based on the intended use and type of liquid being stored. For example, a free-standing fuel tank may have a volume of from 50 gallons to 100 gallons or more. The body 510 can be formed from any suitable non-porous material which is inert and/or non-reactive with the liquids stored in the tank 500. For example, for a fuel tank, the tank body 510 can be formed from a coated metal material, such as aluminum or steel, coated with a protective coating, such as a polyurethane coating, to prevent leaks through the body 510 and/or to prevent portions of the body 510 from corroding due to prolonged exposure to moisture. In some examples, the storage tank 500 is an enclosed structure including, for example, a removable cap 518 configured to seal an opening 524 of the tank 500 to create a fluid-tight sealed structure. In other examples, the tank 500 can include a fluid port and valve configured to receive a nozzle for delivering fluid to and/or extracting fluid from the tank 500. In other examples, the tank 500 can be connected to a network of fluid delivery pipes or conduits which deliver fluid to and extract fluid from the storage tank 500.

As in previously described examples, the moisture sensors 100a, 100b, 100c can be a coaxial moisture sensor formed on a wire, such as the inner electrode 112 shown in FIG. 3. The coaxial moisture sensors 100a, 100b, 100c are configured to be mounted to a portion of the body 510, the location of which is determined based on types of moisture being detected. For example, as shown in FIGS. 8A and 8B, a coaxial moisture sensor 100a can be positioned on an outer surface 526 of the body 510 to detect leaks from the tank 500. In some examples, as shown in FIG. 8A, the coaxial moisture sensor 100a could be positioned to extend across an outer surface of the tank body 510 in an undulating or sinusoidal pattern, which increases the surface area of the tank 500 that can be monitored by a single sensor 100a. The moisture sensor 100a can also be arranged in other patterns including, for example, extending around the storage tank in a helical or spiral pattern, extending axially along the tank 500 in a straight line, or extending around peripheral portions of sides of the tank 500. The moisture sensor 100a can be mounted to an outside surface of the tank 500, so that a moisture or humidity of surrounding air or soil can be measured. In other examples, as shown in FIG. 8B, the moisture sensor 100a can be enclosed by a coating 528 or insulating material and configured to identify both leaks from the tank 500 and moisture ingress through the insulation or coating 528.

With reference to FIG. 8B, the storage tank 500 can further include one or more moisture sensor(s) 100b positioned in the interior volume 520 of the storage tank 500. For example, moisture sensor(s) 100b can be mounted to a portion of an inner surface 522 of the storage tank 500. Some of the moisture sensors 100b can be positioned to measure a level of liquid or fluid F or a volume of fluid F in the tank 500. For example, moisture sensor(s) 100b could be positioned randomly or at discrete distances or depths from the top surface 512 of the tank 500, such as every 2 inches to 4 inches. Measurements from the moisture sensor(s) 100b could detect which sensors 100 are submerged by the fluid F contained in the tank 500 and which sensors 100b are not submerged. Based on this information, the fluid level and fluid volume for fluid F could be calculated.

Moisture sensors 100 in the tank 500 may also be used to determine information about a composition of fluid F contained in the tank 500. For example, impedance measurements from moisture sensor(s) 100c could be used to determine or estimate a concentration of polar and non-polar fluids F. More specifically, the moisture sensors 100c are impedance moisture sensors including the absorbent dielectric material, which is affected by a polarity of liquids absorbed by the material. As such, complex impedance measurements from the moisture sensor 100c can be correlated to a concentration or amount of polar liquid absorbed by the sensors 100c. For example, complex impedance measurements from the moisture sensor 100c can distinguish between a non-polar liquid, such as oil or gasoline, and a polar liquid, such as water. In most cases, a sensor 100c for identifying a concentration of liquid in the tank 500 is positioned near the bottom 514 of the storage tank 500, so that it will be covered with fluid F in most circumstances. For example, a coaxial moisture sensor 100c could be mounted to the inner surface 522 of a bottom 514 of the tank 500. In other examples, the moisture sensor 100c could be positioned on interior surfaces of sides 516 of the tank or other convenient locations. In some examples, moisture sensors 100c for sensing a concentration of liquid could also be positioned at an inflow or outflow port or opening, such as opening 524, to measure concentration of liquids enter or exiting the tank 500.

Figure 9:
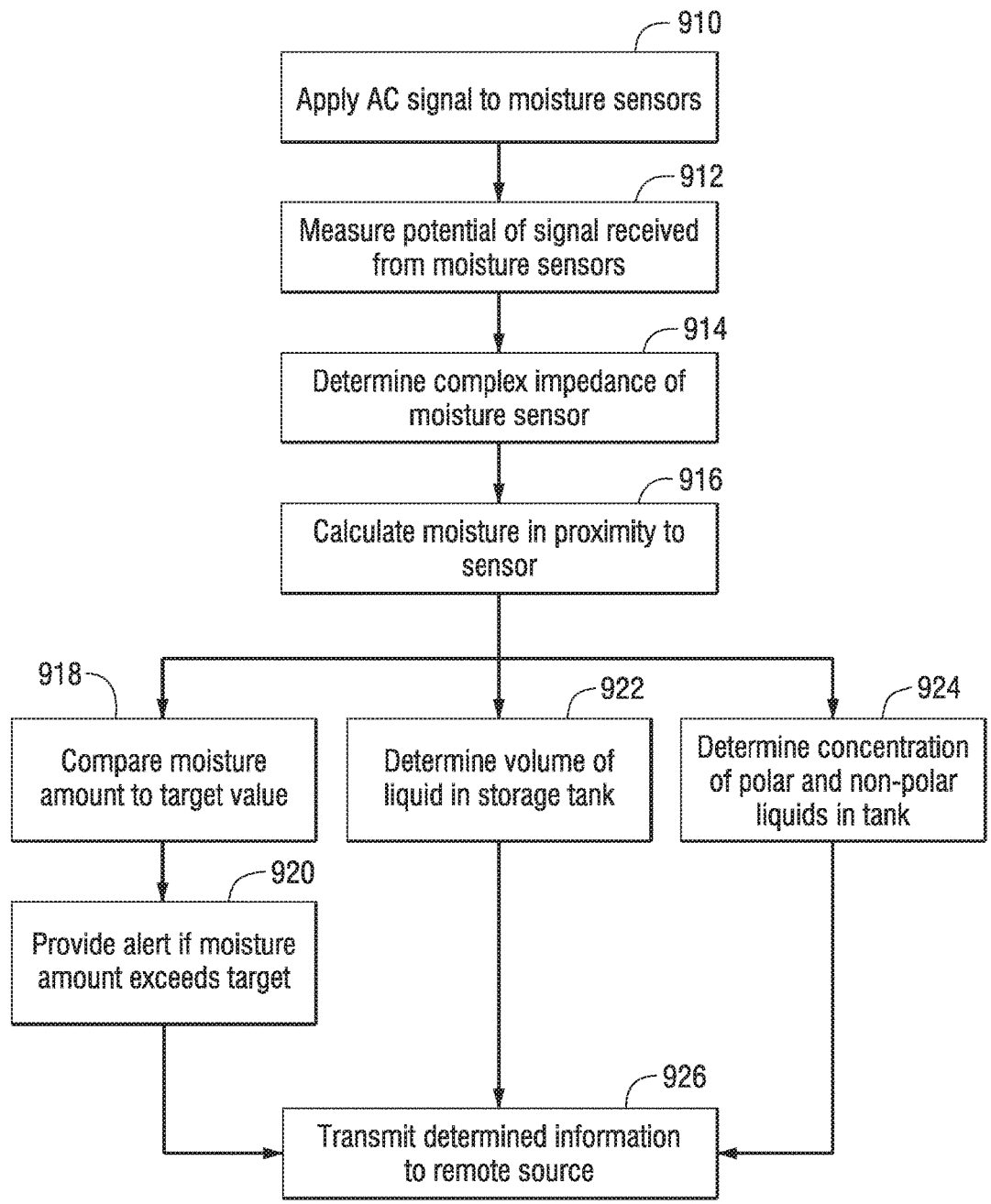
FIG. 9 is a flow chart of a process for monitoring liquids in a storage tank based on data from a moisture sensor, according to an embodiment of the disclosure.

A flow chart illustrating a process for monitoring fluid contents of a storage tank 500 based on information sensed or detected by a moisture sensor(s) is shown in FIG. 9. The moisture sensor(s) can be one or more of the coaxial or planar moisture sensors 100, 200 described herein. The moisture sensors 100, 200 include a dielectric moisture sensitive layer or sheet and are configured to detect, monitor, or identify changes in complex impedance of the moisture sensitive material.

As shown in box 910, a power supply operatively connected to the moisture sensor continually or periodically applies an alternating electrical current to the moisture sensor positioned on a portion of a storage tank. As shown at box 912, an electric measurement device measures an electric potential of a signal received from the moisture sensor in response to the applied current. As shown at box 914, sensor electronics, such as a controller or processor, determine a complex impedance for the moisture sensor based on a comparison of the applied current and measured response. As shown at box 916, an amount of moisture present in proximity to the moisture sensor can be calculated based on the complex impedance.

The controller or processor can determine characteristics of the storage tank and liquids contained therein based on the measured complex impedance. For example, for sensors located on an outer surface of the tank for detecting leaks and/or for sensors inside the tank for detecting moisture ingression into the tank, the detected moisture amount can be compared to a target value for a maximum acceptable amount of moisture, as shown at box 918. When the moisture amount measured by the moisture sensor exceeds the target value, as shown at box 920, the sensor electronics may provide an alert, notification, or warning indicating that leaks into or from the tank have been detected.

For moisture sensors configured to detect a level of fluid in a tank, the sensor electronics can receive moisture information from sensors located at different depths in the tank. Responses from the different sensors can be used to determine which sensors are submerged in liquid and which sensors are not submerged. Based on this determination, as shown at box 922, the controller determines or estimates a volume of liquid in the storage tank and provides the determined or estimated liquid volume to a user.

As shown at box 924, for moisture sensors configured to determine a concentration of polar and non-polar liquids in the tank, a complex impedance measurement for a submerged sensor can be received by the controller. The controller can determine a concentration of polar and non-polar liquids in the storage tank based on a correlation between a measured complex impedance and liquid concentration. For example, the correlation can be based on an experimentally derived model comparing complex impedance for a moisture sensor submerged in a liquid and a concentration of polar and non-polar portions of the liquid. The controller can also cause the determined or estimated concentration value to be provided to the user.

Once information about the storage tank and liquids contained therein is determined, as shown at box 926, the controller can also be configured to transmit detected and calculated information to a remote source, such as a computer device or computer network. For example, information about liquids contained in the tank could be periodically transmitted to a database for recording information about the storage tank and liquids contained therein over time. Information about the tank condition over time could be analyzed to determine, for example, when to schedule repairs and/or to estimate a remaining useful life for the storage tank. In a similar manner, information about a concentration of polar and non-polar liquids over time may be used to determine a shelf life or storage life for fuel in the tank.

Moisture Sensors for Vehicles

According to another aspect of the disclosure, a moisture sensor, such as the coaxial moisture sensor 100, shown in FIG. 3, or the planar moisture sensor 200, shown in FIG. 4, could be configured to identify moisture ingression into areas of a vehicle (e.g., a land, sea, or air vehicle) which are intended to remain free from, or substantially free from, moisture. For example, a moisture sensor could be positioned in or near a portion of a vehicle which is difficult for technicians or mechanics to access to provide an indication about a status or condition of the inaccessible portion of the vehicle. Moisture sensors 100 could also be positioned on or embedded in coated panels of such vehicles to provide information about moisture ingression through the coating, which could be used to determine when a coating has failed and/or when a panel of a vehicle needs to be replaced.

Figure 10A:
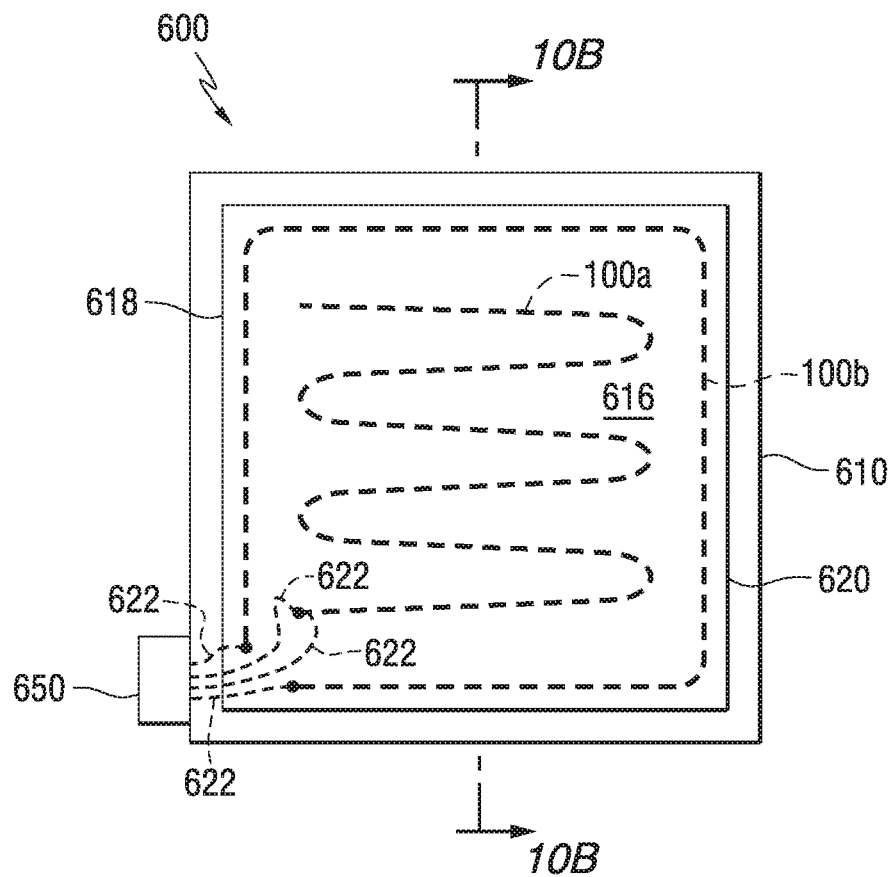
FIG. 10A is top view of a coated panel including a moisture sensor, according to an embodiment of the disclosure.
Figure 10B:
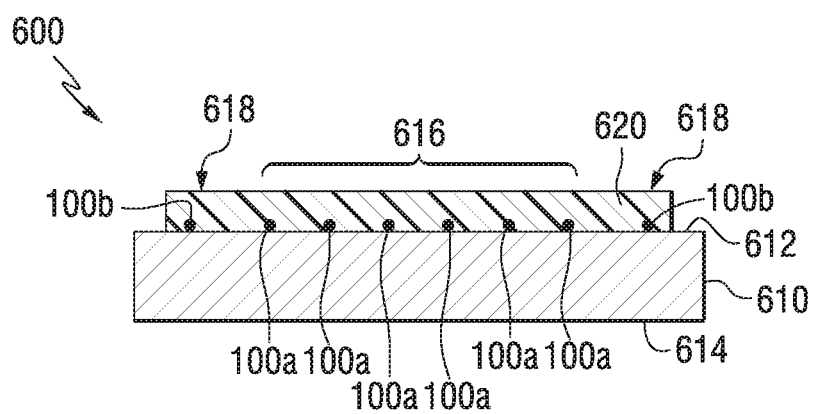
FIG. 10B is a cross sectional view of the panel of FIG. 10A taken along line 10B-10B.

With specific reference to FIGS. 10A and 10B, in one example, coaxial moisture sensors 100a, 100b are provided on a panel 600, such a panel having an opposing top surface 612 and a bottom surface 614. As shown in FIGS. 10A and 10B, the panel 600 is a substantially flat panel. However, the moisture sensors 100a, 100b disclosed herein can also be used with curved panels, angled or inclined panels, or panels having a discontinuous surface. In some instances, the panels may also be bendable or deformable, such that the panels have a flat surface in some environmental conditions and a curved surface in other environmental conditions. As in previous examples, the coaxial moisture sensors 100a, 100b are formed on an inner electrode 112 (shown in FIG. 3) or wire and extend across a surface of the panel 600. The panel 600 can be formed from any rigid structural material, as is used in the manufacture of vehicles, including metals, plastics, ceramics, and/or glass. The moisture sensors 100a, 100b can be positioned to monitor moisture at various portions of the top and/or bottom surfaces 612, 614 of the panel 600. For example, the panel 600 includes a moisture sensor 100a extending across a central portion 616 of the panel 600, such as in a sinusoidal pattern, as shown in FIG. 10A. The panel 600 also includes a moisture sensor 100b positioned along a periphery 618 of the panel 600 to hide the sensor 100b from view and/or for other aesthetic purposes. Moisture sensors 100 positioned near the periphery 618 of panels 600 may also be configured to detect moisture ingression through joints or spaces between adjacent panels 600 of a vehicle, which could cause damage to an interior of the vehicle.

At least a portion of the surface(s) 612, 614 of the panel 600 and moisture sensor 100 can be covered with one or more coating layers 620. For example, the panel 600 can be coated with a moisture resistant layer 620 configured to protect the panel 600 from moisture and corrosion. Layers formed from other coating materials, as are known in the art, such as coatings which reflect solar radiation, scratch resistant layers, heat reflective layers, and/or aesthetic layers (e.g., layers including paints or pigments) can also be applied within the scope of the present disclosure. As shown in FIGS. 10A and 10B, the coating layer(s) 620 extend over the top surface 612 of the panel 600 and enclose or partially enclose portions of the moisture sensors 100a, 100b. For example, during manufacture of the panel 600, the moisture sensors 100a, 100b could be attached to the top surface 612 of the panel 600 in a desired pattern or arrangement with an adhesive, such as a pressure sensitive acrylic adhesive. Once the moisture sensors 100a, 100b are in place, a layer of moisture resistant material could be sprayed or otherwise deposited across the top surface 612, enclosing both the top surface 612 and the moisture sensors 100a, 100b. Moisture measurements from the enclosed moisture sensors 100a, 100b could then be used to identify moisture ingression through the coating layer(s) 620 which could damage other portions of the panel 600.

With specific reference to FIG. 10A, the panel 600 and moisture sensor 100 can further include a control box 650 containing sensor electronics mounted to the panel 600 or to another portion of a vehicle. For example, a wire or lead 622 can extend from electrodes of the moisture sensors 100a, 100b, through a peripheral portion of the coating layer 620, and to the control box 650. As in previously described examples, the control box 650 contains sensor electronics for providing an electrical signal to the moisture sensors 100, receiving a response signal from the sensors 100, and determining complex impedance based on the received signal. In some examples, the control box 650 is connected to a single moisture sensor 100. In other examples, multiple moisture sensors 100, such as sensors 100 located on different panels 600 of a vehicle and/or monitoring different portions of the vehicle, can be electrically connected to a signal control box 650. In that case, the control box 650 can monitor complex impedance at different portions of a panel 600 and/or vehicle to provide information about moisture ingress or standing water at different positions along the panel 600 and/or vehicle.

As described above, the panels 600 and moisture sensors 100a, 100b disclosed herein can be portions of a vehicle. For example, one or more panels 600 could be joined together to form a body of the vehicle. The vehicle can be any land, water, or air vehicle as is known in the art including, for example, automobiles, trucks, all-terrain vehicles (ATVs), airplanes, helicopters, drones (e.g., remotely controlled flying devices), ships, and submarines. A vehicle can include multiple moisture sensors positioned on different panels of the vehicle to monitor a condition of panels and coatings at different positions along the vehicle surface. The vehicle can also include moisture sensors positioned at other hard to reach portions of the vehicle to detect moisture, standing water, or otherwise monitor a condition of the vehicle. For example, moisture sensors could be positioned on an undercarriage of an automobile to identify whether standing water is present which could cause corrosion. In a similar example, moisture sensors could be provided on drones and configured to transmit moisture measurements to remote locations while the drone is in flight. For example, moisture measurements could be shown to a drone pilot to help the pilot monitor a condition of the drone during flight and to identify when moisture is present, which may damage the drone. Similar moisture sensing systems could be provided on hulls of ships, airplane fuselages and similar structures for providing information about moisture ingress and/or areas of standing moisture.

Figure 11:
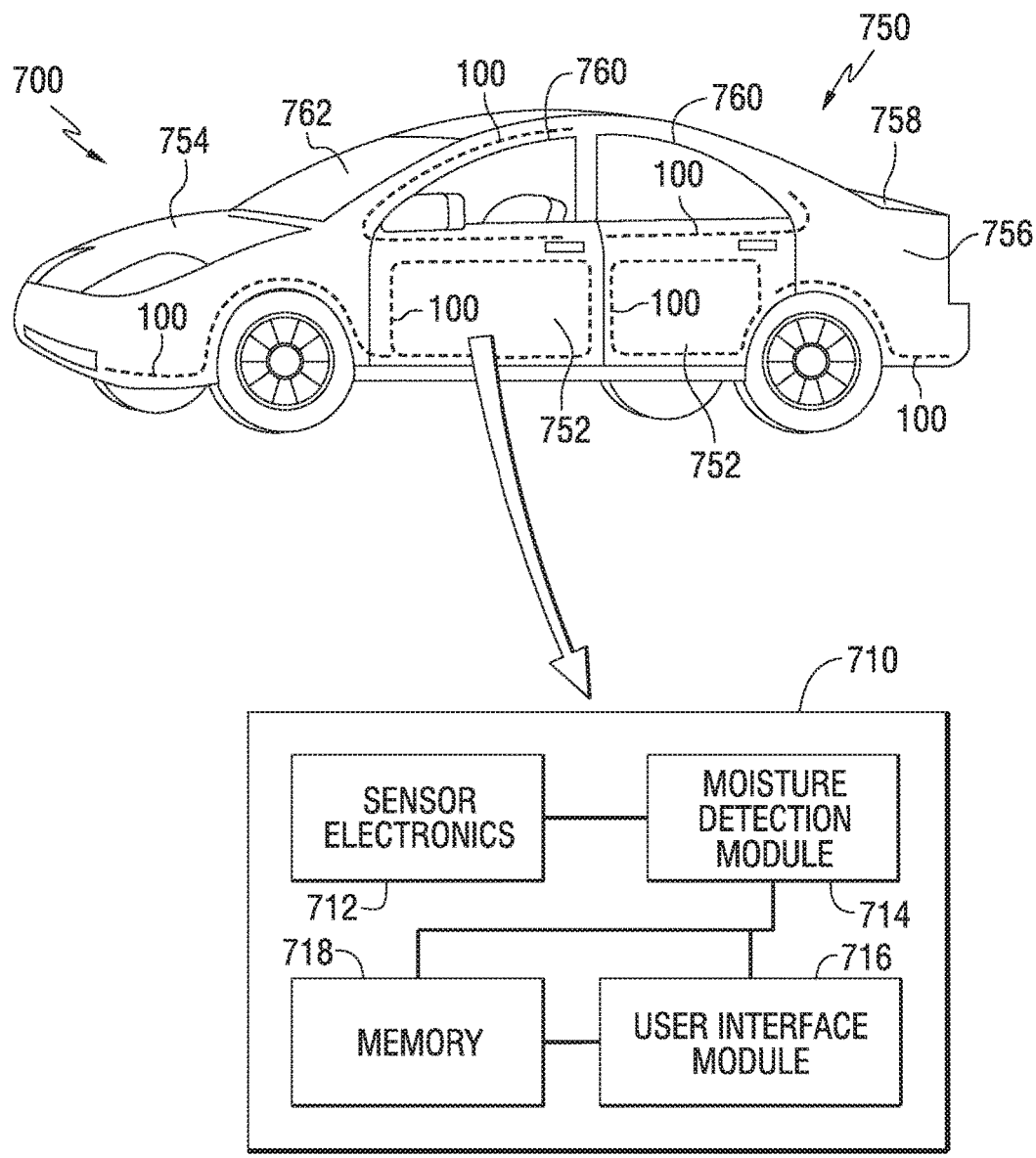
FIG. 11 is a schematic drawing of a vehicle and moisture detecting system including moisture sensors according to an embodiment of the disclosure.

With reference to FIG. 11, a moisture monitoring system 700 for a vehicle 750 is illustrated. The vehicle 750 shown in FIG. 11 is an automobile, though it is understood that similar monitoring systems could be used with many other types of vehicles. The monitoring system 700 includes a plurality of moisture sensors, such as coaxial moisture sensors 100 and/or planar moisture sensors 200, positioned at different locations on the vehicle 750. For example, the vehicle 750 can include panels, such as door panels 752, front body panels 754, and rear body panels 756. The panels 752, 754, 756 can be the coated panels 600 shown in FIGS. 10A and 10B and can include one or more coaxial moisture sensors 100 for detecting moisture ingression through the panels 752, 754, 756. The vehicle 750 can also include one or more moisture sensors 100 positioned in areas which should remain free from or substantially free from moisture to avoid damaging the vehicle 750. For example, it may be acceptable for small amounts of moisture to collect in such areas. However, a volume of the moisture should be small, should evaporate quickly, and should not be permitted to remain in such areas for any longer than a few minutes or hours. In that case, the sensors 100 could be configured to detect standing water and to monitor how long the standing water is present. The system could be configured to provide an alert when detected standing water is present for longer than a predetermined period of time. Such moisture sensors 100 can be positioned in a trunk 758 of the vehicle 750 for detecting whether moisture leaks into and/or collects in portions of the trunk 758. Other moisture sensors 100 could be positioned near seals surrounding windows 760 and windshields 762, as moisture may enter an interior of the vehicle through window openings. The vehicle 750 can also include moisture sensors 100 positioned near portions of a vehicle power train to detect moisture ingression to an engine block, transmission, or drive shaft of the vehicle 750.

As shown schematically in FIG. 11, the moisture sensors 100 are electrically connected to a vehicle computer system 710. The vehicle computer system 710 includes sensor electronics 712 for the sensors 100 and can include, for example, a power supply for applying alternating current to the sensors 100, an electronic measurement device, and one or more controllers for receiving and processing information from the sensors. The system 710 can also include a moisture detection module 714 for receiving information from the sensor electronics 712, analyzing the received information, and drawing conclusions about a status of portions of the vehicle 750. For example, the moisture detection module 714 could consider which moisture sensors 100 of the vehicle 750 detect moisture and which do not. Based on such a consideration, the moisture detection module 714 could determine whether the vehicle is safe to operate, whether maintenance is required, or whether one or more of the sensors may be malfunctioning or providing incorrect readings. The moisture detection module 714 could also be configured to emit warnings, notifications, or alerts based on the determined status of the vehicle and/or detected moisture. The vehicle computer system 710 can also include a user feedback or user interface module 716 configured to receive alerts, warnings, and notifications from the moisture detection module 714 and provide them to a user, such as a driver. In some examples, alerts, warnings, or notifications could also be stored on system memory 718, so that they can be reviewed by a technician or mechanic at a later date.

In view of the foregoing description and Examples, the present invention thus relates inter alia to the subject matter of the following clauses though being not limited thereto.

Clause 1: An insulated pipe comprising: an elongated tube comprising a first end, a second end, and a sidewall extending therebetween; an insulating member at least partially enclosing a portion of the pipe sidewall, the insulating member comprising at least one channel extending through at least a portion of the insulating member; and at least one coaxial moisture sensor positioned within at least a portion of the channel configured to sense moisture in the channel, the at least one coaxial moisture sensor comprising: a dielectric member comprising a sleeve defining a center hole formed from an absorbent dielectric polymer material; an outer electrode electrically connected with an outer surface of the dielectric member, the outer electrode comprising a moisture permeable sleeve which permits moisture to pass to the dielectric member; and an inner electrode comprising a wire extending through the center hole of and electrically connected with an inner surface of the dielectric member, wherein the dielectric member is in electrical contact with the first and second electrodes and maintains the first and the second electrodes spaced from one another.

Clause 2: The insulated pipe of clause 1, further comprising sensor electronics operatively connected to the electrodes of the moisture sensor to measure an electrical property of the moisture sensor to determine an amount of moisture absorbed by the dielectric member, wherein the sensor electronics comprise: a power source for applying alternating electrical current to at least one of the first electrode and the second electrode; and an electrical measurement device configured to measure a complex impedance (ohms) of the dielectric member.

Clause 3: The insulated pipe of clause 2, wherein the sensor electronics further comprise a controller operatively connected to the power source and to the electrical measurement device, and wherein the controller is configured to cause the power source to periodically apply the alternating current to at least one of the electrodes.

Clause 4: The insulated pipe of clause 3, wherein the controller is further configured to determine an amount of moisture within the channel based on the measured complex impedance.

Clause 5: The insulated pipe of any of clauses 1 to 4, wherein the coaxial moisture sensor is wrapped around at least a portion of the elongated tube within the at least one channel in a helical arrangement.

Clause 6: The insulated pipe of any of clauses 1 to 5, wherein the coaxial moisture sensor extends axially along at least a portion of the elongated tube within the at least one channel in a straight line.

Clause 7: The insulated pipe of any of clauses 1 to 6, wherein the insulating material comprises one or more of open cell foam insulation, closed cell foam insulation, fiber glass insulation, cellulose insulation, cotton batts, and wool batts.

Clause 8: The insulated pipe of any of clauses 1 to 7, wherein the dielectric polymer material comprises one or more of nylon 4-6, nylon 6, nylon 6-6, nylon 6-12, nylon 11, polyamideimide, polybenzimidazole, polyethersulfone, or polysulfone.

Clause 9: The insulated pipe of any of clauses 1 to 8, wherein the electrodes comprise one or more of ruthenium, rhodium, palladium, silver, osmium, iridium, platinum, gold, copper, tin, nickel, chromium, or aluminum, or mixtures, alloys, or combinations thereof.

Clause 10: The insulated pipe of any of clauses 1 to 9, wherein a maximum outer diameter of a cross-section of the sensor along a longitudinal axis of the sensor is 0.060 inch or less.

Clause 11: A container configured to enclose objects in a low moisture environment, the container comprising: a top portion, a bottom portion, and sides extending between the top portion and the bottom portion thereof; and at least one coaxial moisture sensor enclosed within a cavity defined by the top portion, bottom portion, and sides, the coaxial moisture sensor comprising: a dielectric member comprising a sleeve defining a center hole formed from an absorbent dielectric polymer material; an outer electrode electrically connected with an outer surface of the dielectric member, comprising a porous sleeve for permitting moisture to pass through the sleeve; and an inner electrode comprising a wire extending through the center hole of and electrically connected with an inner surface of the dielectric member, wherein the dielectric member is in electrical contact with the first and second electrodes and maintains the first and the second electrodes spaced from one another.

Clause 12: The container of clause 11, further comprising sensor electronics operatively connected to the electrodes of the moisture sensor to measure an electrical property of the moisture sensor to determine an amount of moisture absorbed by the dielectric member, wherein the sensor electronics comprise: a power source for applying alternating electrical current to at least one of the first electrode and the second electrode; and an electrical measurement device configured to measure a complex impedance (ohms) of the dielectric member.

Clause 14: The container of clause 13, wherein the sensor electronics further comprises a controller electronically connected to the power source and to the electric measurement device, and wherein the controller is configured to: cause the power source to periodically apply the alternating current to at least one of the electrodes; receive a complex impedance measurement from the electrical measurement device in response to the applied alternating current; and detect a presence of moisture in the cavity of the container based on the measured complex impedance.

Clause 15: The container of clause 12 or clause 13, wherein the container is a housing of a portable electronic device, and further comprising electronic circuitry of the electronic device positioned in the cavity of the container and in electrical communication with the sensor electronics of the moisture sensor, wherein the electronic circuitry of the portable electronic device is configured to one or more of automatically power down, automatically save data to computer memory of the electronic circuitry, or transmit data to a remote source when the measured complex impedance exceeds a predetermined value.

Clause 15: The container of any of clauses 11 to 13, wherein the container comprises a liquid storage tank, and wherein the at least one moisture sensor is positioned to detect at least one of leaks from the storage tank and/or moisture ingress into the storage tank.

Clause 16: The container of clauses 11 to 13 wherein the container comprises a liquid storage tank, and further comprising a controller in electrical communication with the moisture sensor configured to: receive the measured complex impedance from the moisture sensor; and determine a concentration of polar and non-polar liquids in the storage tank based on the measured complex impedance.

Clause 17: The container of any of clauses 11 to 16, wherein the container comprises a liquid storage tank and a plurality of equidistantly spaced coaxial moisture sensors on an inner surface of a side of the container, and further comprising a controller configured to: receive the measured complex impedance from the plurality of moisture sensors; and determine a volume of liquid in the storage tank based on the measured complex impedance of the plurality of moisture sensors.

Clause 18: The container of any of clauses 11 to 17, wherein the at least one moisture sensor has a maximum outer diameter of 0.060 inch or less.

Clause 19: A method for detecting moisture in insulation surrounding a pipe, the method comprising: applying an alternating electrical current to a coaxial moisture sensor positioned within a channel extending through insulation at least partially surrounding a pipe, the moisture sensor comprising: a dielectric member comprising a sleeve defining a center hole formed from an absorbent dielectric polymer material, a first electrode surrounding at least a portion of the dielectric member, and a second electrode extending through a portion of the center hole of the dielectric member; continually or periodically measuring a complex impedance of the dielectric member with sensor electronics connected to the first and/or the second electrodes; and determining an amount of moisture within the insulation based on the measured complex impedance.

Whereas particular embodiments of this invention have been described above for purposes of illustration, it will be evident to those skilled in the art that numerous variations of the details of the present invention may be made without departing from the invention as defined in the appended claims.

The invention claimed is:
1. An insulated pipe comprising:
an elongated tube comprising a first end, a second end, and a sidewall extending therebetween, the sidewall comprising an inner surface and an outer surface;
an insulating member at least partially covering a portion of the outer surface of the sidewall of the elongated tube, the insulating member comprising at least one channel extending through at least a portion of the insulating member; and
at least one coaxial moisture sensor positioned within at least a portion of the channel configured to sense moisture in the channel, the at least one coaxial moisture sensor comprising:
a dielectric member comprising a sleeve defining a center hole formed from an absorbent dielectric polymer material;
an outer electrode electrically connected with an outer surface of the dielectric member, the outer electrode comprising a moisture permeable sleeve which permits moisture to pass to the dielectric member; and
an inner electrode comprising a wire extending through the center hole of and electrically connected with an inner surface of the dielectric member,
wherein the dielectric member is in electrical contact with the inner electrode and the outer electrode and maintains the inner electrode and the outer electrode spaced from one another.

2. The insulated pipe of claim 1, further comprising sensor electronics operatively connected to the electrodes of the moisture sensor to measure an electrical property of the moisture sensor to determine an amount of moisture absorbed by the dielectric member, wherein the sensor electronics comprise:
a power source for applying alternating electrical current to at least one of the inner electrode electrode and the outer electrode; and
an electrical measurement device configured to measure a complex impedance (ohms) of the dielectric member.

3. The insulated pipe of claim 2, wherein the sensor electronics further comprise a controller operatively connected to the power source and to the electrical measurement device, and wherein the controller is configured to cause the power source to periodically apply the alternating current to at least one of the electrodes.

4. The insulated pipe of claim 3, wherein the controller is further configured to determine an amount of moisture within the channel based on the measured complex impedance.

5. The insulated pipe of claim 1, wherein the coaxial moisture sensor is wrapped around at least a portion of the outer surface of the elongated tube within the at least one channel in a helical arrangement.

6. The insulated pipe of claim 1, wherein the coaxial moisture sensor extends axially along at least a portion of the outer surface of the elongated tube within the at least one channel in a straight line.

7. The insulated pipe of claim 1, wherein the insulating member comprises one or more of open cell foam insulation, closed cell foam insulation, fiber glass insulation, cellulose insulation, cotton batts, and wool batts.

8. The insulated pipe of claim 1, wherein the dielectric polymer material comprises one or more of nylon 4-6, nylon 6, nylon 6-6, nylon 6-12, nylon 11, polyamide-imide, polybenzimidazole, polyethersulfone, or polysulfone.

9. The insulated pipe of claim 1, wherein the electrodes comprise one or more of ruthenium, rhodium, palladium, silver, osmium, iridium, platinum, gold, copper, tin, nickel, chromium, or aluminum, or mixtures, alloys, or combinations thereof.

10. The insulated pipe of claim 1, wherein a maximum outer diameter of a cross-section of the sensor along a longitudinal axis of the sensor is 0.060 inch or less.

11. A container enclosing a cavity configured to enclose objects in a low moisture environment, the container comprising:
 a top portion, a bottom portion, and sides extending between the top portion and the bottom portion thereof, each of the top portion, the bottom portion, and the sides comprising an inner surface and an outer surface; and
 at least one coaxial moisture sensor mounted to and extending over at least a portion of at least one of the inner surface or the outer surface of at least one of the top portion, the bottom portion, or the sides, the coaxial moisture sensor comprising:
  a dielectric member comprising a sleeve defining a center hole formed from an absorbent dielectric polymer material;
  an outer electrode electrically connected with an outer surface of the dielectric member, comprising a porous sleeve for permitting moisture to pass through the sleeve; and
  an inner electrode comprising a wire extending through the center hole of and electrically connected with an inner surface of the dielectric member,
  wherein the dielectric member is in electrical contact with the inner electrode and the outer electrode and maintains the inner electrode and the outer electrode spaced from one another.

12. The container of claim 11, further comprising sensor electronics operatively connected to the electrodes of the moisture sensor to measure an electrical property of the moisture sensor to determine an amount of moisture absorbed by the dielectric member, wherein the sensor electronics comprise:
 a power source for applying alternating electrical current to at least one of the inner electrode and the outer electrode; and
 an electrical measurement device configured to measure a complex impedance (ohms) of the dielectric member.

13. The container of claim 12, wherein the sensor electronics further comprises a controller electronically connected to the power source and to the electric measurement device, and wherein the controller is configured to:
 cause the power source to periodically apply the alternating current to at least one of the electrodes;
 receive a complex impedance measurement from the electrical measurement device in response to the applied alternating current; and
 detect a presence of moisture in the cavity of the container based on the measured complex impedance.

14. The container of claim 12, wherein the container is a housing of a portable electronic device, and further comprising electronic circuitry of the electronic device positioned in the cavity of the container and in electrical communication with the sensor electronics of the moisture sensor,
 wherein the electronic circuitry of the portable electronic device is configured to one or more of automatically power down, automatically save data to computer memory of the electronic circuitry, or transmit data to a remote source when the measured complex impedance exceeds a predetermined value.

15. The container of claim 11, wherein the container comprises a liquid storage tank, and wherein the at least one moisture sensor is positioned to detect at least one of leaks from the storage tank and/or moisture ingress into the storage tank.

16. The container of claim 11, wherein the container comprises a liquid storage tank, and further comprising a controller in electrical communication with the moisture sensor configured to:
 receive the measured complex impedance from the moisture sensor; and
 determine a concentration of polar and non-polar liquids in the storage tank based on the measured complex impedance.

17. The container of claim 11, wherein the container comprises a liquid storage tank and a plurality of equidistantly spaced coaxial moisture sensors on an inner surface of a side of the container, and further comprising a controller configured to:
 receive the measured complex impedance from the plurality of moisture sensors; and
 determine a volume of liquid in the storage tank based on the measured complex impedance of the plurality of moisture sensors.

18. The container of claim 11, wherein the at least one moisture sensor has a maximum outer diameter of 0.060 inch or less.

19. A method for detecting moisture in insulation surrounding a pipe, the method comprising:
 applying an alternating electrical current to a coaxial moisture sensor positioned within a channel extending through insulation at least partially covering an outer surface of the pipe, the moisture sensor comprising: a dielectric member comprising a sleeve defining a center hole formed from an absorbent dielectric polymer material, a first electrode surrounding at least a portion of the dielectric member, and a second electrode extending through a portion of the center hole of the dielectric member;
 continually or periodically measuring a complex impedance of the dielectric member with sensor electronics connected to the first and/or the second electrodes; and
 determining an amount of moisture within the insulation based on the measured complex impedance.

* * * * *